(12) United States Patent
Nash et al.

(10) Patent No.: US 8,485,958 B2
(45) Date of Patent: *Jul. 16, 2013

(54) SYSTEMS AND METHODS FOR SEPARATING CONSTITUENTS OF BIOLOGIC LIQUID MIXTURES

(75) Inventors: John E. Nash, Chester Springs, PA (US); William T. Fisher, Schwenksville, PA (US)

(73) Assignee: Kensey Nash Corporation, Exton, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/568,629

(22) Filed: Aug. 7, 2012

(65) Prior Publication Data

US 2013/0029829 A1    Jan. 31, 2013

Related U.S. Application Data

(63) Continuation of application No. 12/949,781, filed on Nov. 19, 2010, now Pat. No. 8,317,672.

(51) Int. Cl.
*B01D 21/26* (2006.01)
*B04B 11/04* (2006.01)

(52) U.S. Cl.
USPC .......... 494/37; 494/2; 494/3; 494/10; 494/26; 494/43; 494/56; 604/6.04

(58) Field of Classification Search
USPC .............. 494/2, 3, 10, 26, 43, 45, 37, 56; 604/6.01–6.06; 210/782
See application file for complete search history.

(56) References Cited

U.S. PATENT DOCUMENTS

| | | |
|---|---|---|
| 347,702 A | 8/1886 | Evans |
| 1,429,320 A | 9/1922 | Bouillon |
| 1,921,181 A | 8/1933 | Fawcett |
| 2,023,762 A | 12/1935 | Fawcett |
| 2,596,616 A | 5/1952 | Strezynski |
| 2,822,126 A | 2/1958 | Cohn et al. |
| 2,822,315 A | 2/1958 | Cohn et al. |
| 2,873,910 A | 2/1959 | Steinacker |
| 2,906,450 A | 9/1959 | Lang et al. |
| 2,906,451 A | 9/1959 | Tullis et al. |
| 2,906,452 A | 9/1959 | Tullis |
| 2,940,662 A | 6/1960 | Applegate |

(Continued)

FOREIGN PATENT DOCUMENTS

WO    9400169    1/1994

OTHER PUBLICATIONS

International Search Report dated May 30, 2012 re Application No. PCT/US2011/001922.

*Primary Examiner* — Michael Marcheschi
*Assistant Examiner* — Timothy Cleveland
(74) *Attorney, Agent, or Firm* — Caesar, Rivise, Bernstein, Cohen & Pokotilow, Ltd.

(57) ABSTRACT

Centrifuges are useful to, among other things, remove red blood cells from whole blood and retain platelets and other factors in a reduced volume of plasma. Platelet rich plasma (PRP) can be obtained rapidly and is ready for immediate injection into the host. Embodiments may include valves, operated manually or automatically, to open ports that discharge the excess red blood cells and the excess plasma while retaining the platelets and other factors. High speeds used allow simple and small embodiments to be used at the patient's side during surgical procedures. The embodiments can also be used for the separation of liquids or slurries in other fields such as, for example, the separation of pigments or lubricants.

13 Claims, 18 Drawing Sheets

U.S. PATENT DOCUMENTS

Figure 1A:
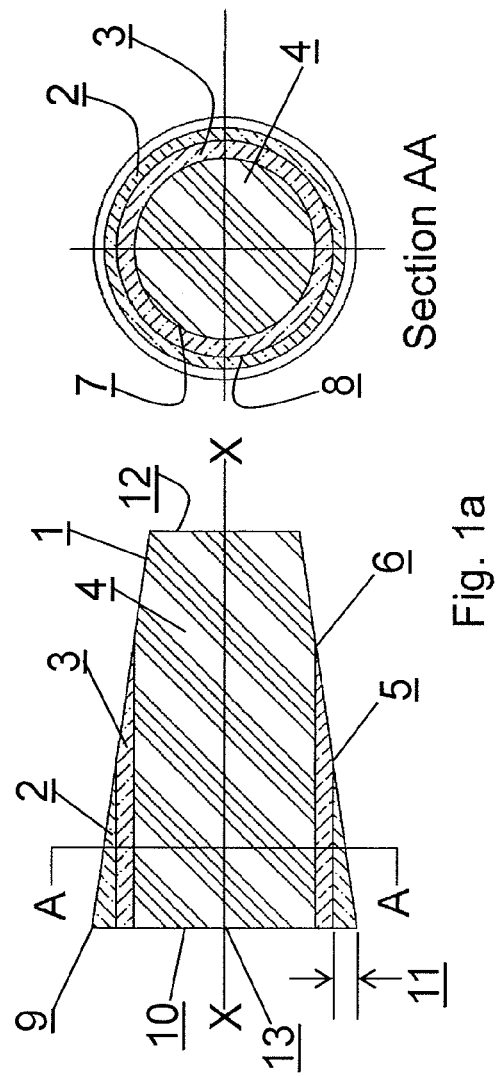

| Patent No. | | Date | Inventor |
|---|---|---|---|
| 3,085,407 | A | 4/1963 | Tomlinson |
| 3,092,582 | A | 6/1963 | Lacker |
| 3,096,283 | A | 7/1963 | Hein |
| 3,104,225 | A | 9/1963 | DiBenedetto |
| 3,145,713 | A | 8/1964 | Latham, Jr. |
| 3,239,136 | A | 3/1966 | Hein |
| 3,244,362 | A | 4/1966 | Hein |
| 3,249,295 | A | 5/1966 | Childs |
| 3,304,990 | A | 2/1967 | Ontko et al. |
| 3,332,614 | A | 7/1967 | Webster et al. |
| 3,482,771 | A | 12/1969 | Thylefors |
| 3,655,123 | A | 4/1972 | Judson et al. |
| 3,675,846 | A | 7/1972 | Drucker |
| 3,780,936 | A | 12/1973 | Bush |
| 3,825,177 | A | 7/1974 | Kohlstette et al. |
| 3,908,893 | A | 9/1975 | Williams |
| 3,955,755 | A | 5/1976 | Breillatt, Jr. et al. |
| 3,982,691 | A | 9/1976 | Schlutz |
| 4,056,225 | A | 11/1977 | Hein, Jr. |
| 4,081,129 | A | 3/1978 | Stroucken |
| 4,086,924 | A | 5/1978 | Latham, Jr. |
| 4,111,355 | A | 9/1978 | Ishimaru |
| 4,132,349 | A | 1/1979 | Khoja et al. |
| 4,226,669 | A | 10/1980 | Vilardi |
| 4,285,464 | A | 8/1981 | Latham, Jr. |
| 4,303,193 | A | 12/1981 | Latham, Jr. |
| 4,304,357 | A | 12/1981 | Schoendorfer |
| 4,332,350 | A | 6/1982 | McClellan |
| 4,332,351 | A | 6/1982 | Kellogg et al. |
| 4,341,343 | A | 7/1982 | Beckman |
| 4,392,846 | A | 7/1983 | Novoselac et al. |
| 4,421,503 | A | 12/1983 | Latham, Jr. et al. |
| 4,425,112 | A | 1/1984 | Ito |
| 4,530,691 | A | 7/1985 | Brown |
| 4,629,564 | A | 12/1986 | Pinato |
| 4,636,193 | A | 1/1987 | Cullis |
| 4,684,361 | A | 8/1987 | Feldman et al. |
| 4,753,729 | A | 6/1988 | Schoendorfer et al. |
| 4,776,964 | A | 10/1988 | Schoendorfer et al. |
| 4,813,923 | A | 3/1989 | Johansson |
| 4,816,151 | A | 3/1989 | Schoendorfer et al. |
| 4,828,716 | A | 5/1989 | McEwen et al. |
| 4,846,781 | A | 7/1989 | Knelson |
| 4,854,933 | A | 8/1989 | Mul |
| 4,859,333 | A | 8/1989 | Panzani |
| 4,879,031 | A | 11/1989 | Panzani |
| 4,889,524 | A | 12/1989 | Fell et al. |
| 4,911,833 | A | 3/1990 | Schoendorfer et al. |
| 4,944,883 | A | 7/1990 | Schoendorfer et al. |
| 4,959,158 | A | 9/1990 | Meikrantz |
| 5,007,892 | A | 4/1991 | Columbus |
| 5,032,288 | A | 7/1991 | Columbus et al. |
| 5,034,135 | A | 7/1991 | Fischel |
| 5,039,401 | A | 8/1991 | Columbus et al. |
| 5,053,127 | A | 10/1991 | Schoendorfer et al. |
| 5,076,911 | A | 12/1991 | Brown et al. |
| 5,100,372 | A | 3/1992 | Headley |
| 5,104,526 | A | 4/1992 | Brown et al. |
| 5,147,186 | A | 9/1992 | Buckholtz |
| 5,149,432 | A | 9/1992 | Lavin |
| 5,188,583 | A | 2/1993 | Guigan |
| 5,254,075 | A | 10/1993 | Nemoto et al. |
| 5,254,076 | A | 10/1993 | Chow et al. |
| 5,254,248 | A | 10/1993 | Nakamura |
| 5,267,936 | A | 12/1993 | Miachon |
| 5,316,667 | A | 5/1994 | Brown et al. |
| 5,322,620 | A | 6/1994 | Brown et al. |
| 5,354,256 | A | 10/1994 | Knelson |
| 5,387,174 | A | 2/1995 | Rochat |
| 5,405,308 | A | 4/1995 | Headley et al. |
| 5,441,475 | A | 8/1995 | Storruste et al. |
| 5,480,378 | A | 1/1996 | Weis-Fogh et al. |
| 5,514,070 | A | 5/1996 | Pages |
| 5,573,678 | A | 11/1996 | Brown et al. |
| 5,585,007 | A | 12/1996 | Antanavich et al. |
| 5,603,845 | A | 2/1997 | Holm |
| 5,607,830 | A | 3/1997 | Biesel et al. |
| 5,628,915 | A | 5/1997 | Brown et al. |
| 5,632,893 | A | 5/1997 | Brown et al. |
| 5,643,594 | A | 7/1997 | Dorian et al. |
| 5,674,173 | A | 10/1997 | Hlavinka et al. |
| 5,728,040 | A | 3/1998 | Schill et al. |
| 5,733,446 | A | 3/1998 | Holm |
| 5,738,784 | A | 4/1998 | Holm et al. |
| 5,738,792 | A | 4/1998 | Schoendorfer |
| 5,741,428 | A | 4/1998 | Holm |
| 5,750,039 | A | 5/1998 | Brown et al. |
| 5,776,336 | A | 7/1998 | Holm |
| 5,788,662 | A | 8/1998 | Antanavich et al. |
| 5,792,344 | A | 8/1998 | Holm |
| 5,795,489 | A | 8/1998 | Holm |
| 5,807,492 | A | 9/1998 | Brown et al. |
| 5,824,230 | A | 10/1998 | Holm et al. |
| 5,830,352 | A | 11/1998 | Holm |
| 5,849,178 | A | 12/1998 | Holm et al. |
| 5,851,169 | A | 12/1998 | Meresz et al. |
| 5,853,600 | A | 12/1998 | McNeal et al. |
| 5,858,253 | A | 1/1999 | Holm |
| 5,873,810 | A | 2/1999 | Holm et al. |
| 5,935,432 | A | 8/1999 | Holm |
| 5,939,319 | A | 8/1999 | Hlavinka et al. |
| 5,955,026 | A | 9/1999 | Holm et al. |
| 5,958,253 | A | 9/1999 | Holm |
| 5,961,842 | A | 10/1999 | Min et al. |
| 5,964,724 | A | 10/1999 | Rivera et al. |
| 5,980,760 | A | 11/1999 | Min et al. |
| 5,993,370 | A | 11/1999 | Brown et al. |
| 6,007,472 | A | 12/1999 | Schill et al. |
| 6,007,725 | A | 12/1999 | Brown |
| 6,027,655 | A | 2/2000 | Holm |
| 6,027,657 | A | 2/2000 | Min et al. |
| 6,051,146 | A | 4/2000 | Green et al. |
| 6,063,297 | A | 5/2000 | Antanavich et al. |
| 6,099,740 | A | 8/2000 | Holm et al. |
| 6,123,655 | A | 9/2000 | Fell |
| 6,123,687 | A | 9/2000 | Simonyi et al. |
| 6,132,598 | A | 10/2000 | Hvid et al. |
| 6,214,338 | B1 | 4/2001 | Antanavich et al. |
| 6,228,017 | B1 | 5/2001 | Brown |
| 6,241,649 | B1 | 6/2001 | Zanella et al. |
| 6,296,602 | B1 | 10/2001 | Headley |
| 6,299,784 | B1 | 10/2001 | Biesel |
| 6,302,836 | B1 | 10/2001 | North, Jr. |
| 6,348,031 | B1 | 2/2002 | Unger et al. |
| 6,387,263 | B1 | 5/2002 | Bhaskar et al. |
| 6,398,972 | B1 | 6/2002 | Blasetti et al. |
| 6,416,456 | B2 | 7/2002 | Zanella et al. |
| 6,475,175 | B1 | 11/2002 | Rivera et al. |
| 6,511,411 | B1 | 1/2003 | Brown |
| 6,530,871 | B1 | 3/2003 | Mackel et al. |
| 6,544,162 | B1 | 4/2003 | Van Wie et al. |
| 6,689,042 | B2 | 2/2004 | Unger et al. |
| 6,716,151 | B2 | 4/2004 | Panzani et al. |
| 6,716,187 | B1 | 4/2004 | Jorgensen et al. |
| 6,719,901 | B2 | 4/2004 | Dolecek et al. |
| 6,733,433 | B1 | 5/2004 | Fell |
| 6,814,862 | B2 | 11/2004 | Biesel |
| 6,835,316 | B2 | 12/2004 | Dolecek |
| 6,835,353 | B2 | 12/2004 | Smith et al. |
| 6,855,119 | B2 | 2/2005 | Rivera et al. |
| 6,899,666 | B2 | 5/2005 | Brown |
| 6,905,612 | B2 | 6/2005 | Dorian et al. |
| RE38,757 | E | 7/2005 | Wells et al. |
| 6,946,079 | B1 | 9/2005 | Holm |
| 6,962,560 | B2 | 11/2005 | Grewel |
| 6,964,646 | B1 | 11/2005 | Biesel |
| 6,979,307 | B2 | 12/2005 | Beretta et al. |
| 6,982,038 | B2 | 1/2006 | Dolecek et al. |
| 7,001,323 | B2 | 2/2006 | Panzani et al. |
| 7,029,430 | B2 | 4/2006 | Hlavinka et al. |
| 7,033,501 | B1 | 4/2006 | Bhaskar et al. |
| 7,037,428 | B1 | 5/2006 | Robinson et al. |
| 7,060,017 | B2 | 6/2006 | Collier |
| 7,060,018 | B2 | 6/2006 | Skinkle et al. |
| 7,074,173 | B2 | 7/2006 | Kohlstette et al. |
| 7,081,082 | B2 | 7/2006 | Scholz et al. |
| 7,134,991 | B2 | 11/2006 | Rivalier et al. |

| | | | | | |
|---|---|---|---|---|---|
| 7,156,800 B2 | 1/2007 | Panzani et al. | 7,708,152 B2 | 5/2010 | Dorian et al. |
| 7,179,391 B2 | 2/2007 | Leach et al. | 7,740,760 B2 | 6/2010 | Coull et al. |
| 7,195,606 B2 | 3/2007 | Ballin | 7,745,106 B2 | 6/2010 | Beretta et al. |
| 7,204,795 B2 | 4/2007 | Himmen et al. | 7,771,590 B2 | 8/2010 | Leach et al. |
| 7,223,346 B2 | 5/2007 | Dorian et al. | 7,780,860 B2 | 8/2010 | Higgins et al. |
| 7,252,758 B2 | 8/2007 | Dolecek et al. | 7,789,245 B2 | 9/2010 | Westberg et al. |
| 7,306,555 B2 | 12/2007 | Dolecek et al. | 7,803,279 B2 | 9/2010 | Coull et al. |
| 7,311,849 B2 | 12/2007 | Panzani et al. | 7,806,276 B2 | 10/2010 | Leach et al. |
| 7,314,441 B2 | 1/2008 | Collier | 7,811,463 B2 | 10/2010 | Dolecek et al. |
| 7,347,932 B2 | 3/2008 | Holmes et al. | 7,824,559 B2 | 11/2010 | Dorian et al. |
| 7,347,948 B2 | 3/2008 | Dolecek et al. | 7,828,709 B2 | 11/2010 | Sweat |
| 7,353,415 B2 | 4/2008 | Coull et al. | 7,832,566 B2 | 11/2010 | Leach et al. |
| 7,364,657 B2 | 4/2008 | Mandrusov et al. | 7,833,185 B2 | 11/2010 | Felt et al. |
| 7,374,678 B2 | 5/2008 | Leach et al. | 7,837,884 B2 | 11/2010 | Dorian et al. |
| 7,407,472 B2 | 8/2008 | Skinkle et al. | 7,845,499 B2 | 12/2010 | Higgins et al. |
| 7,413,652 B2 | 8/2008 | Dolecek et al. | 7,857,744 B2 | 12/2010 | Langley et al. |
| 7,470,371 B2 | 12/2008 | Dorian et al. | 7,866,485 B2 | 1/2011 | Dorian et al. |
| 7,520,402 B2 | 4/2009 | Ellsworth et al. | 7,867,159 B2 | 1/2011 | Dolecek et al. |
| 7,553,413 B2 | 6/2009 | Dorian et al. | 2005/0054506 A1 | 3/2005 | Bradley |
| 7,694,828 B2 | 4/2010 | Swift et al. | 2008/0128367 A1 | 6/2008 | Rochat |

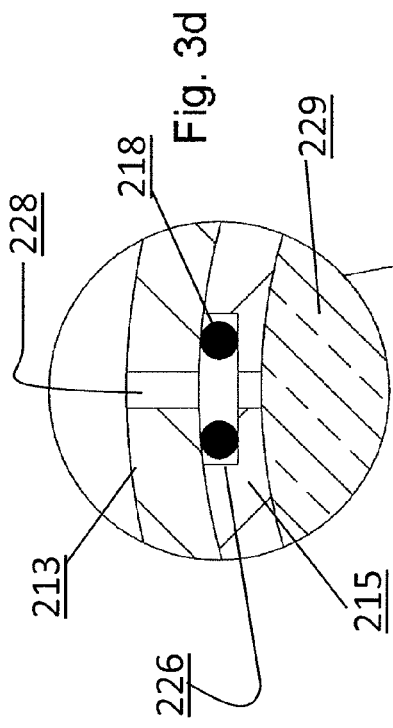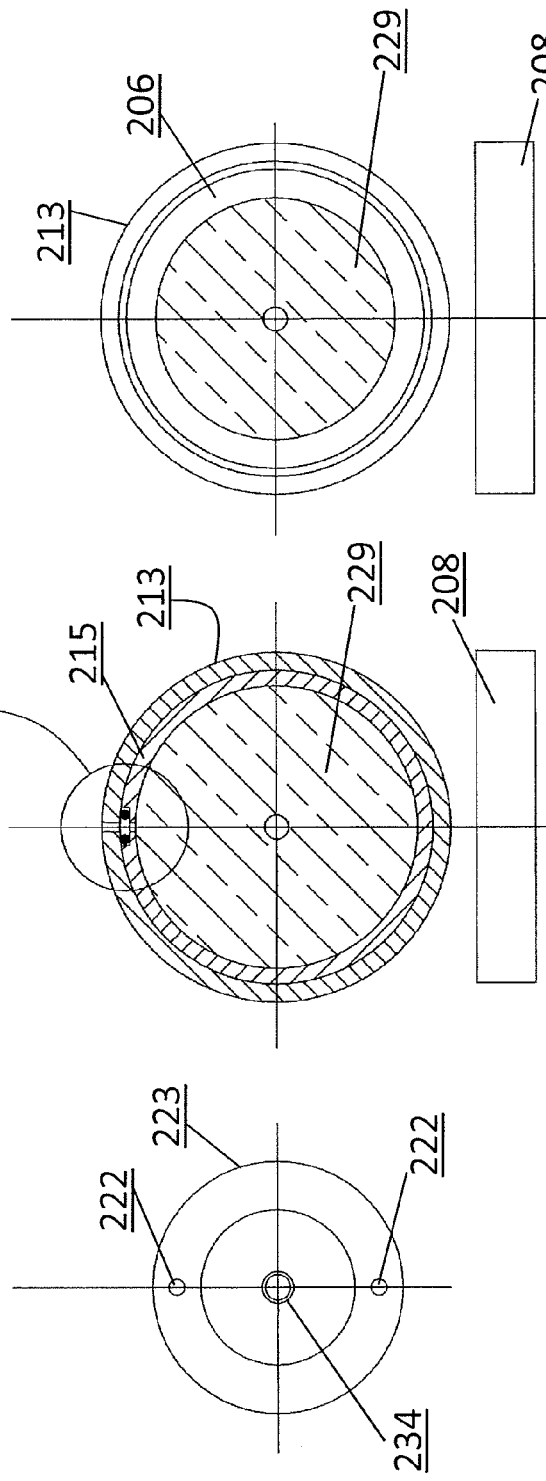

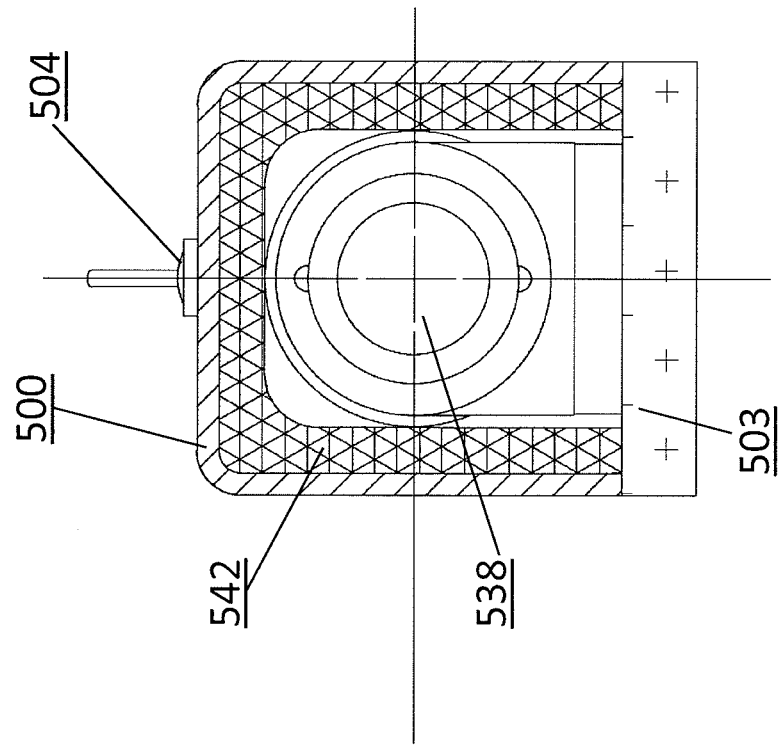
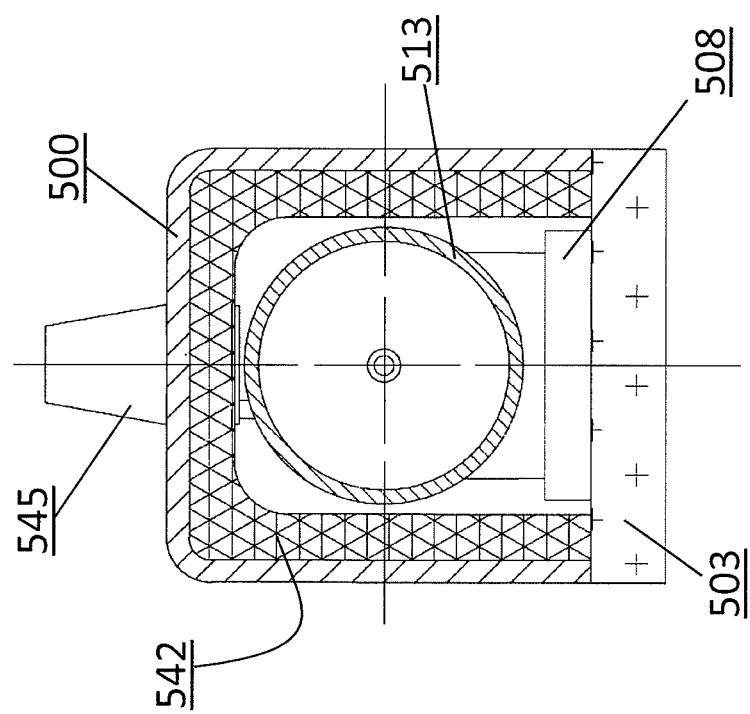
Fig. 18 A
Fig. 18 B

SYSTEMS AND METHODS FOR SEPARATING CONSTITUENTS OF BIOLOGIC LIQUID MIXTURES

CROSS REFERENCE TO RELATED APPLICATIONS

This continuation application claims the benefit under 35 U.S.C. §120 of application Ser. No. 12/949,781, U.S. Pat. No. 8,317,672, filed on Nov. 19, 2010 and entitled "Centrifuge" and the entire contents of this application are expressly incorporated herein by reference thereto.

BACKGROUND OF THE INVENTION

1. Field of the Invention

The present invention pertains to centrifuges.

2. Discussion of Related Art

Fluids, such as whole blood or various other biological fluids are suspensions and can be separated into their constituent parts or fractions. For example, whole blood comprises four main fractions, red blood cells, white blood cells, platelets and plasma, that can be separated based on their different specific gravities in a device such as a centrifuge. An anti-coagulated whole blood sample may be placed in a test tube, or other similar device, which is then spun in a centrifuge at a specified speed. The generated centrifugal force separates the blood into the different fractions based on their relative specific gravities. The red blood cells are on the bottom, plasma, is on the top with the intermediate specific gravity white blood cells and platelets intermediate to the other two fractions. Various other biological fluids may be separated as well. For example, nucleated cells may be separated and extracted from bone marrow or adipose tissue derived samples.

It is desirable to isolate the different fractions of whole blood for differing medicinal purposes. The platelets can be obtained in preparations of platelet rich plasma (PRP) or platelet concentrates (PC). Platelets contain growth factors (e.g. PDGF, TGF-β, and others), which may initiate, aid in or accelerate various bodily functions, including but not limited to angiogenesis, wound healing, and osteogenesis. Administering autologous platelets to an injury site may improve the healing response by using a patient's own platelets without the risk of infection by using blood products from another donor source.

Various systems exist for the production of PRP/PC. Some use specialized test tubes, U.S. Pat. Nos. 7,179,391 and 7,520,402, that can include floats, tubing and/or gel materials of specific densities. Other systems use specialized double syringes, for example those found in U.S. Pat. Nos. 6,716,187 and 7,195,606. These test tubes and syringes must be centrifuged in a specialized large centrifuge for a specified time, typically 10-30 minutes, and then by delicate handling and extraction or decanting procedures produce the desired PRP/PC. The consistency of these preparations can vary depending on the operator's skill level. Other systems, for example U.S. Pat. No. 6,982,038, contain specialized centrifuge chambers and complicated control systems to produce the PRP/PC in about 30 minutes. All of these systems provide PRP/PC of differing platelet concentrations depending on the method used. A major drawback to these methods is the need for an expensive piece of capital equipment which limits the utility to facilities that have the funds and space available. These methods also require considerable operator skills to complete the procedures necessary to obtain the PRP/PC.

The ability to produce PRP/PC from a patient's own blood at the point of care without the need for complex, expensive equipment and difficult procedures would facilitate the clinical utility of PRP/PC. Therefore the objects of this invention include among other things providing an apparatus and method for processing a patient's own blood at the point of care in a short period of time that is self contained, battery operated, small and or portable, inexpensive, easy to use, reproducible, able to separate many cellular populations, and disposable without the need for additional centrifugation equipment

SUMMARY OF THE INVENTION

In accordance with the invention, a single use, sterile, self-contained, compact, easy to use centrifugal separation unit provides for quick, reliable platelet concentration from whole blood. The resultant PRP/PC can be immediately used for application to the patient. The unit is suitable for office, operating room, emergency use, or military field hospital use.

The disposable self-contained PRP separator features a motor with a drive axis, the drive axis being coaxial with the central or longitudinal axis of the blood separation chamber (BSC) assembly. The motor can have the capacity to rotate the BSC at speeds in the range 10,000 to 25,000 RPM for several minutes. Power can be supplied to the motor through a battery or other power pack. The power can be connected through a switch and even small dry cell batteries will have sufficient capacity to complete the separation process. The BSC and motor/battery are fully enclosed in an outer container that includes an access port to the BSC to which a standard syringe can be attached. Alternatively the BSC can be rotated by non-electrical means such as an air driven turbine or spring drive. It could also include a magnetic or mechanical coupling to an external drive motor, or any source of energy that may be available at the surgical site for example in the surgical suite or on location during a trauma procedure, such as at a "MASH" compound.

In a first embodiment the BSC assembly features a barrel that may be cylindrical or tapered, an end cap incorporating passageways and a tubular extension, and in some embodiments a piston or bladder, that between them define the BSC. A sleeve sliding over the outer diameter of the end cap acts as the moving part of two valve assemblies, each valve featuring a recess in the outer surface of the end cap and an O-ring in the recess. Passages within the end cap lead from the BSC to the recess centers, and two ports in the sleeve align with the recess centers in a 3 position sequence. The two ports in the sleeve are positioned so that they do not align with the two recess centers in the end cap at the same time. In sequence the sleeve selects a first port open, then both ports closed, and then a second port open. The ports are opened in a stepwise motion, but could be opened proportionally. The sleeve is operated by a knob connected to a slidable collar through a bearing assembly so that the knob does not rotate during operation of the motor.

Anti-coagulated blood is injected through the tubular extension in order to fill the BSC. The sleeve is in a first position where both ports on the sleeve do not align with either of the recesses in the end cap. The motor is actuated and the BSC rotates to create a centrifugal force on the blood thereby separating it into its components with the red blood cells closest to the inner wall of the BSC with the white blood cells lining the red blood cell layer toward the center, followed by the platelets and then plasma filling the center. In other words, the centrifugation yields concentric stratified constituent layers of the mixture, with adjacent concentric stratified constituent layers defining a mixture interface. After a centrifugation period of about 1 minute or less the sleeve is moved to a second position in which the first port in the sleeve aligns with the recess in the end cap. This port communicates with the layer of red blood cells against the inner wall. The red blood cells will exit the chamber through this port due to pressure generated by the centrifugal force. As red blood cells exit the separator, the volume is replaced by air entering through the tubular extension in the end cap. The air forms a column in the center of the chamber that grows larger as more volume is replaced. It is also conceived that without an air inlet vent, that continued rotation and evacuation of the red blood cells will result in a vacuum core being formed, as the blood is degassed and possibly drawing vapor from the liquid due to the reduced pressure at the center of rotation. After a substantial amount, preferably the majority, of the red blood cells are discharged from the blood separator volume, the sleeve is moved to a third position to close the first port and open the second port. This is done before the layer of platelets in the volume can exit the first port. The passage to the second recess in the end cap of the device is precisely positioned away from the center axis to remove a volume of plasma from the BSC without disturbing the platelet layer. As plasma leaves the chamber, air replaces the volume through the tubular extension and the column of air in the center of the BSC continues to grow in diameter. When the diameter of the air column encompasses the second passage entrance, no more plasma can exit the chamber and the concentration process is thereby automatically ended. In the case where there is a vacuum core created, the concentration process would automatically end in a similar manner, as the vacuum core encounters the second passage entrance. The device is turned off and the platelet concentrate is ready for use.

Another embodiment uses a flexible bladder lining the interior of the BSC. The solid end of the BSC includes a hole for air to enter around the exterior of the flexible bladder. The end cap axis tubular extension includes an airtight valve. This embodiment operates in the same manner except that it does not deliberately introduce air into contact with the blood sample. During the centrifugation cycle while red blood cells and then plasma are exiting the chamber, air enters the opposite side of the chamber thus collapsing the flexible bladder. Due to the pressure generated in the liquid by centrifugal force, the sack collapses into a "W" shape with the open ends of the "W" facing toward the end of the chamber opposite the end with the air bleed hole. As more plasma exits the chamber the middle of the "W" reaches the second passage in the end cap and closes the passage off thus automatically ending the cycle.

Another embodiment replaces the flexible bladder with a piston and spring: as red blood cells (RBCs) exit the valve ports, the piston moves towards the end cap encouraged by the spring.

It is further disclosed that the system of the subject invention may incorporate an automatic shutoff mechanism to seal the port(s) based upon certain conditions. For example, one such mechanism can incorporate a flowable separator gel of an intermediate specific gravity selected to be between an undesired element, e.g. red blood cells, and a desired therapeutic element, e.g. platelets. The separator gel viscosity is designed so that it will not pass through the small exit port at the centrifuge speed employed in the blood separation centrifuge. Upon activation of the centrifuge, the separator gel would create a distinct layer and barrier between the outer red blood cell layer, located near the periphery of the axis of rotation, and the platelet poor layer which would be located closer to the center axis of the centrifuge rotation. The separator gel automatically plugs the first port when all of the red blood cells have exited. As a further example, the automatic shut-off of the first port can be accomplished with a solid damper, or vent flap, also constructed of a material with a specifically targeted intermediate specific gravity. Upon initial operation, the damper would open and separate away from the vent hole based upon its specific gravity and attempt to position itself at a location between the red blood cells and the platelets. As in the previous example, once the red blood cells have fully exited the system, the damper would seal the vent hole and effectively prevent the platelet rich fluid from exited the system. As yet another example, plastic beads such as microspheres with the desired intermediate specific gravity could also be pre-located within the centrifuge chamber. The beads would be sized appropriately to plug the exit port after the undesirable element, e.g. red blood cells, exited the system.

In another embodiment, the BSC can be made of a clear (transparent) material so that the progress of the red blood cell removal can be observed through a clear window in the outer case. This can allow for precise timing for closing the first port to end the exiting of the red blood cells.

Another embodiment accomplishes the concentration through precise timing of the valve opening/closing sequence and the starting and stopping of the motor.

BRIEF DESCRIPTIONS OF THE DRAWINGS

Figure 1B:
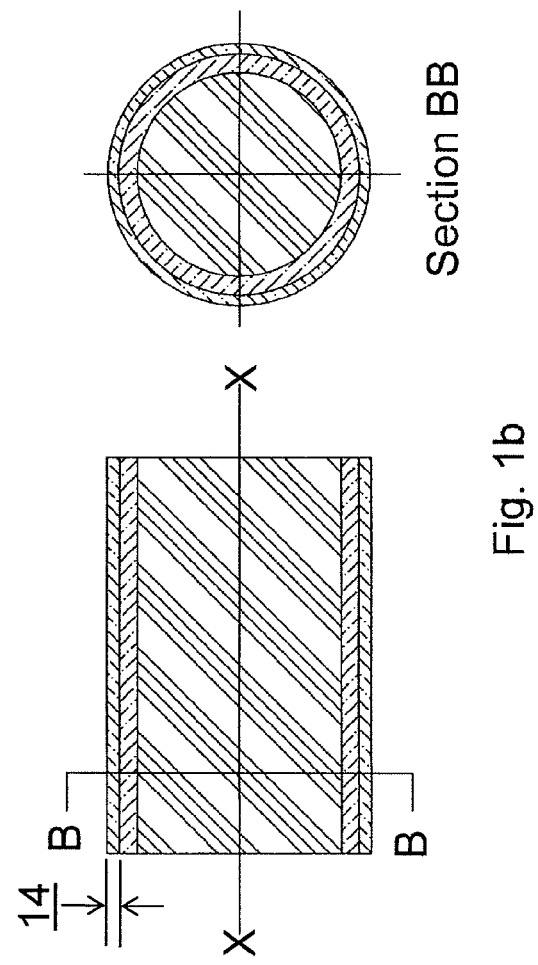

FIGS. 1a and 1b: Principle of operation

Figure 2:
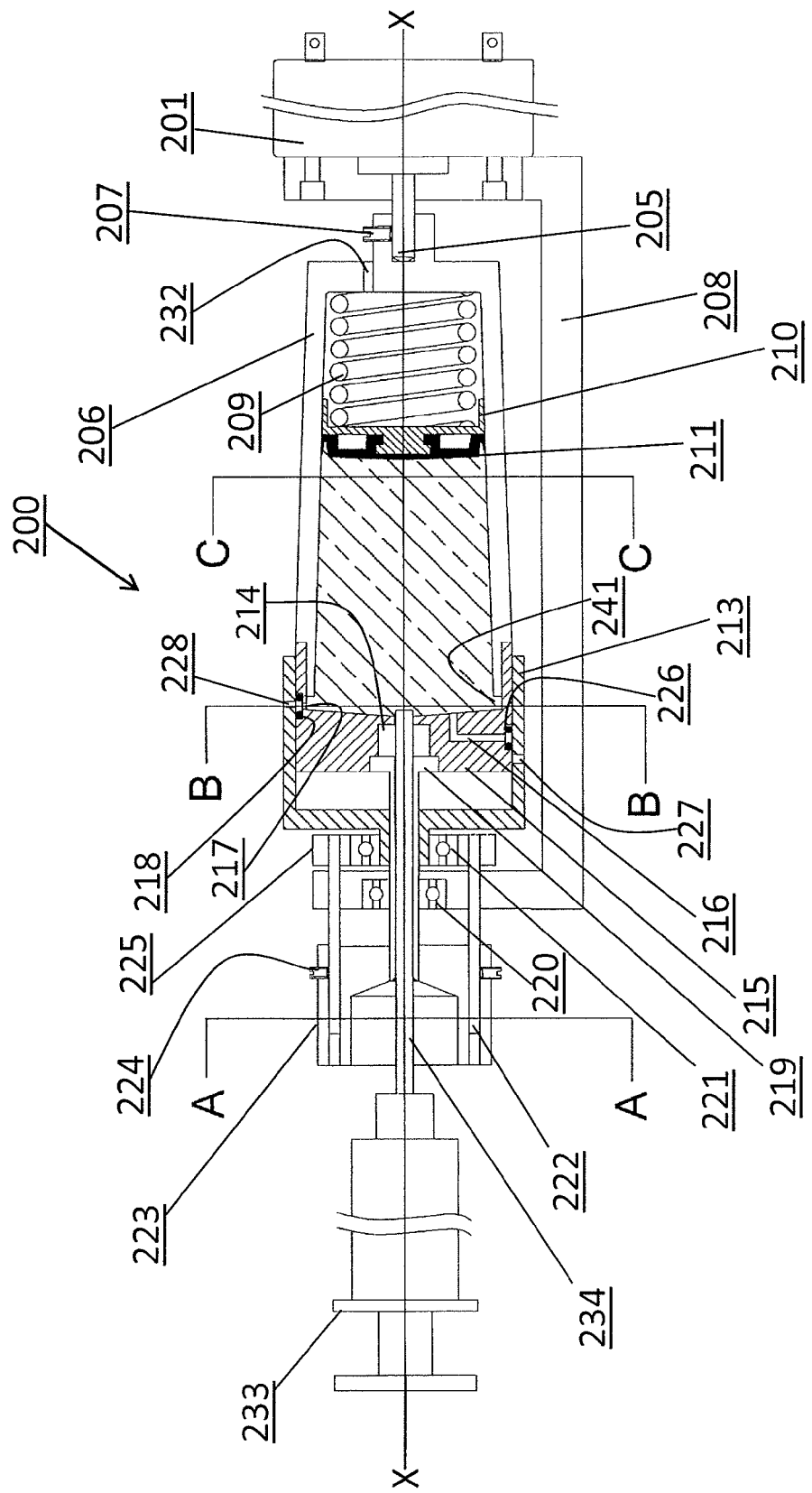

FIG. 2: Centrifuge with spring loaded piston in tapered chamber, charge position, RBC valve open, Plasma valve closed (Longitudinal part section)

FIGS. 3a, 3b, 3c, and 3d show transverse sections of the centrifuge with spring loaded piston in tapered chamber, (transverse sections of FIG. 2), and enlarged details of the RBC valve components used in all devices shown in FIGS. 2, 4, 5, 6, 7, 9,10,11, 12, 14, 15, 16, 17, and 18.

Figure 4:
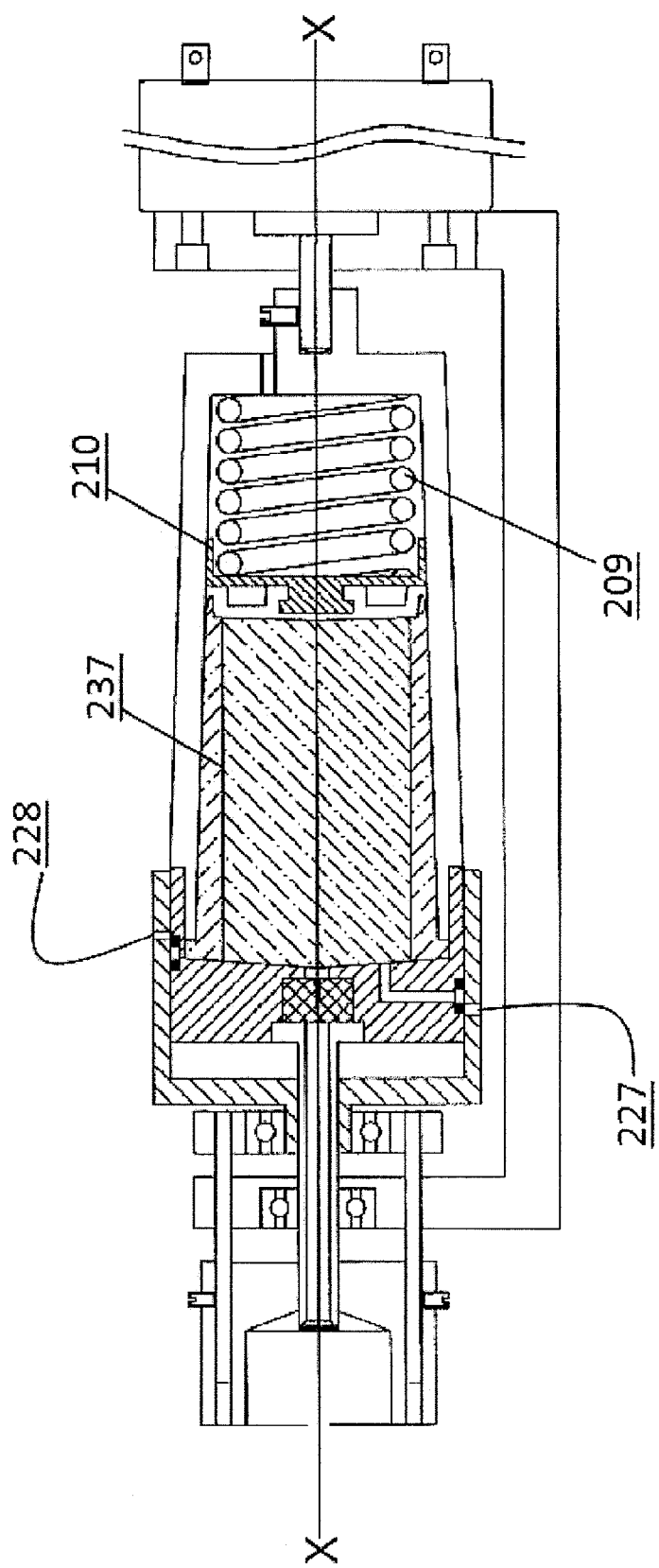

FIG. 4: Centrifuge with spring-loaded piston in tapered chamber, spin-down, RBCs separated from plasma, both valves closed (Longitudinal part section).

Figure 5:
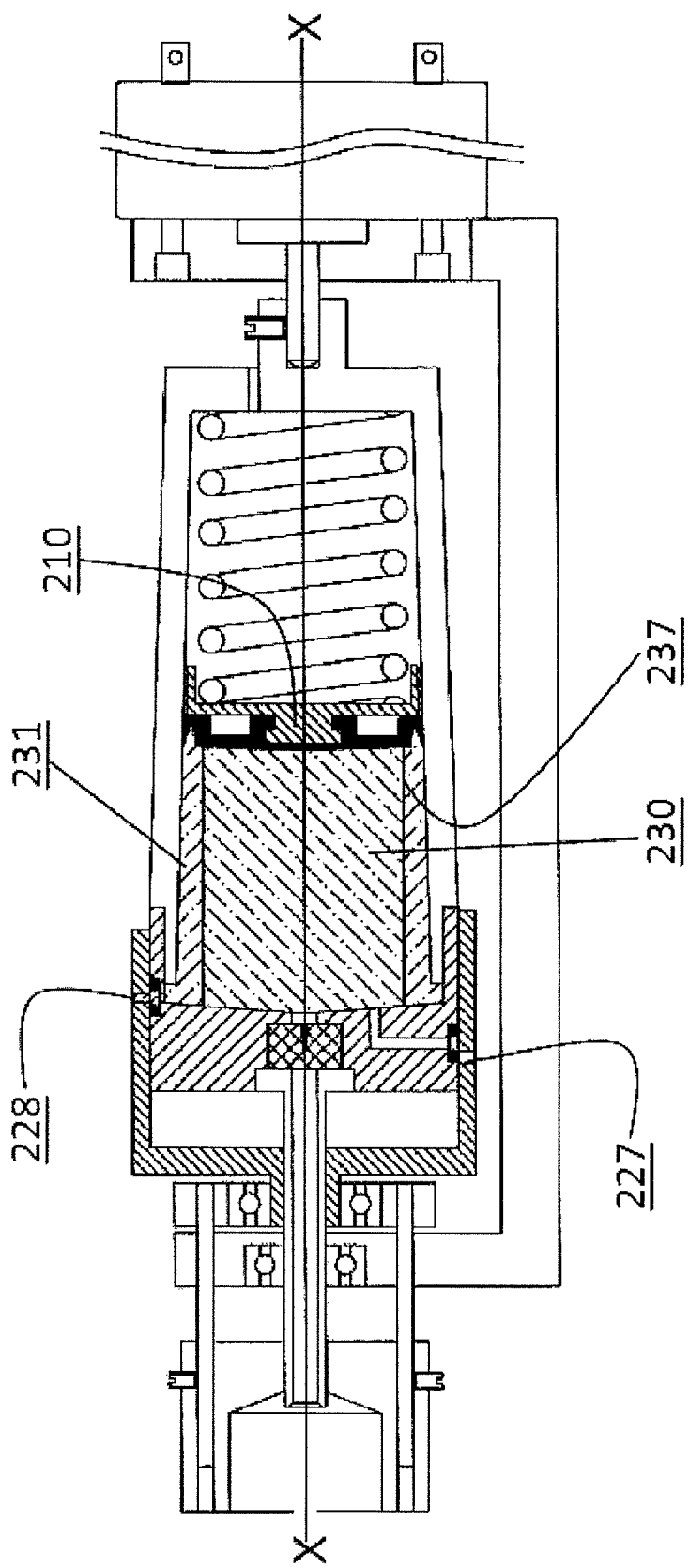

FIG. 5: Centrifuge with spring-loaded piston in tapered chamber, mid position, RBC valve open and RBCs being dumped, plasma valve closed (Longitudinal part section).

Figure 6:
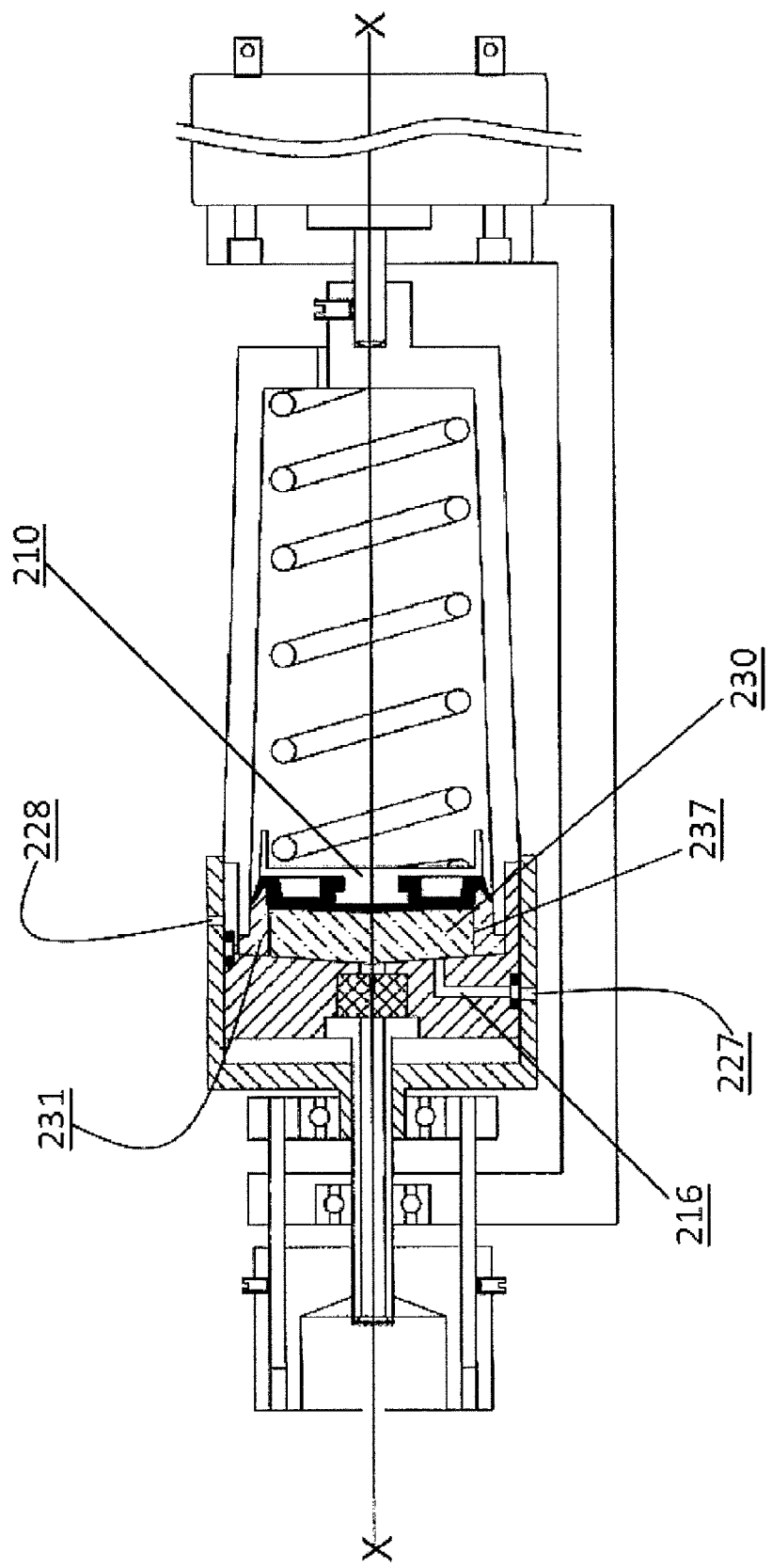

FIG. 6: Centrifuge with spring-loaded piston in tapered chamber, final position, RBC valve closed, plasma valve open and most of plasma dumped (Longitudinal part section).

Figure 7:
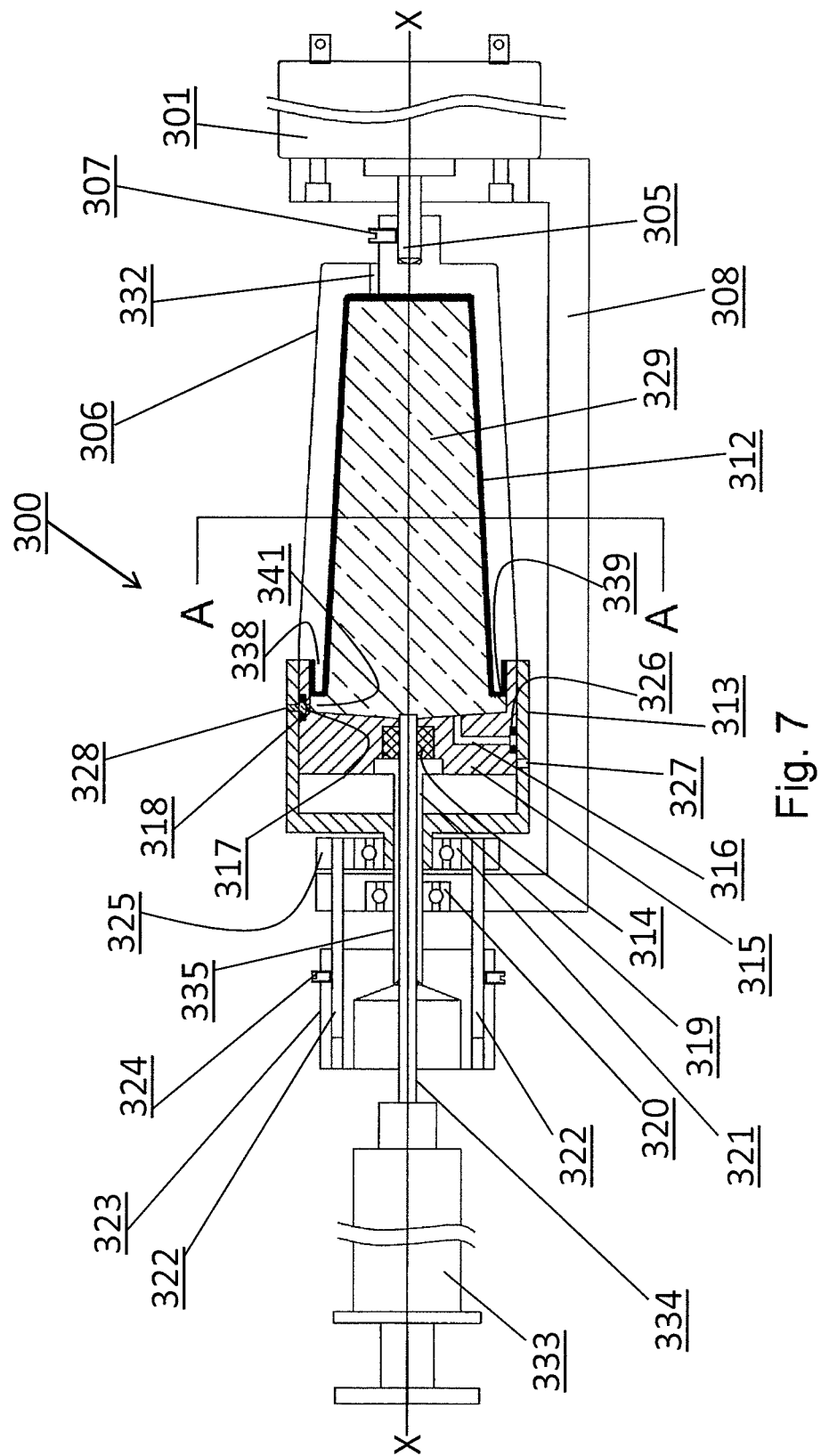

FIG. 7: Centrifuge with bladder chamber, charge position, RBC valve open, plasma valve closed (Longitudinal part section).

Figure 8:
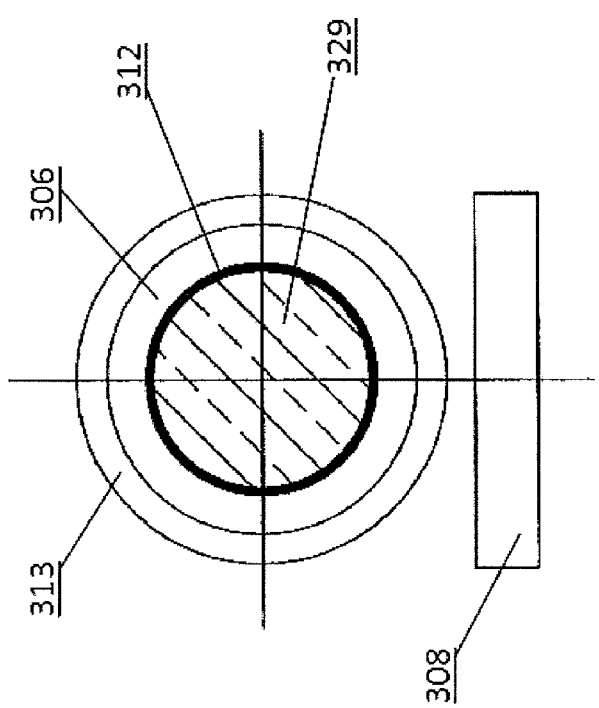

FIG. 8: Centrifuge with bladder chamber, charge position, (transverse section of FIG. 7.)

Figure 9:
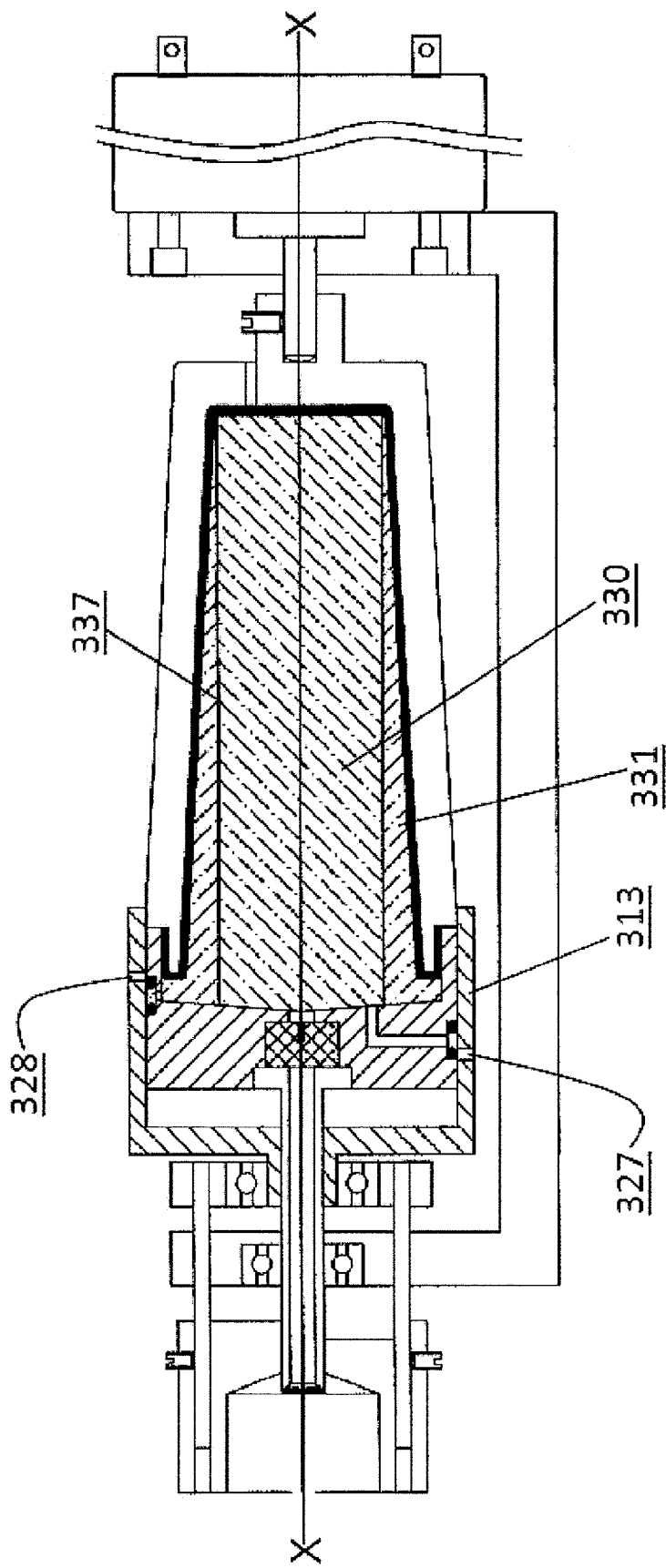

FIG. 9: Centrifuge with bladder chamber, spin-down, RBCs separated from plasma, both valves closed, (longitudinal part section).

Figure 10:
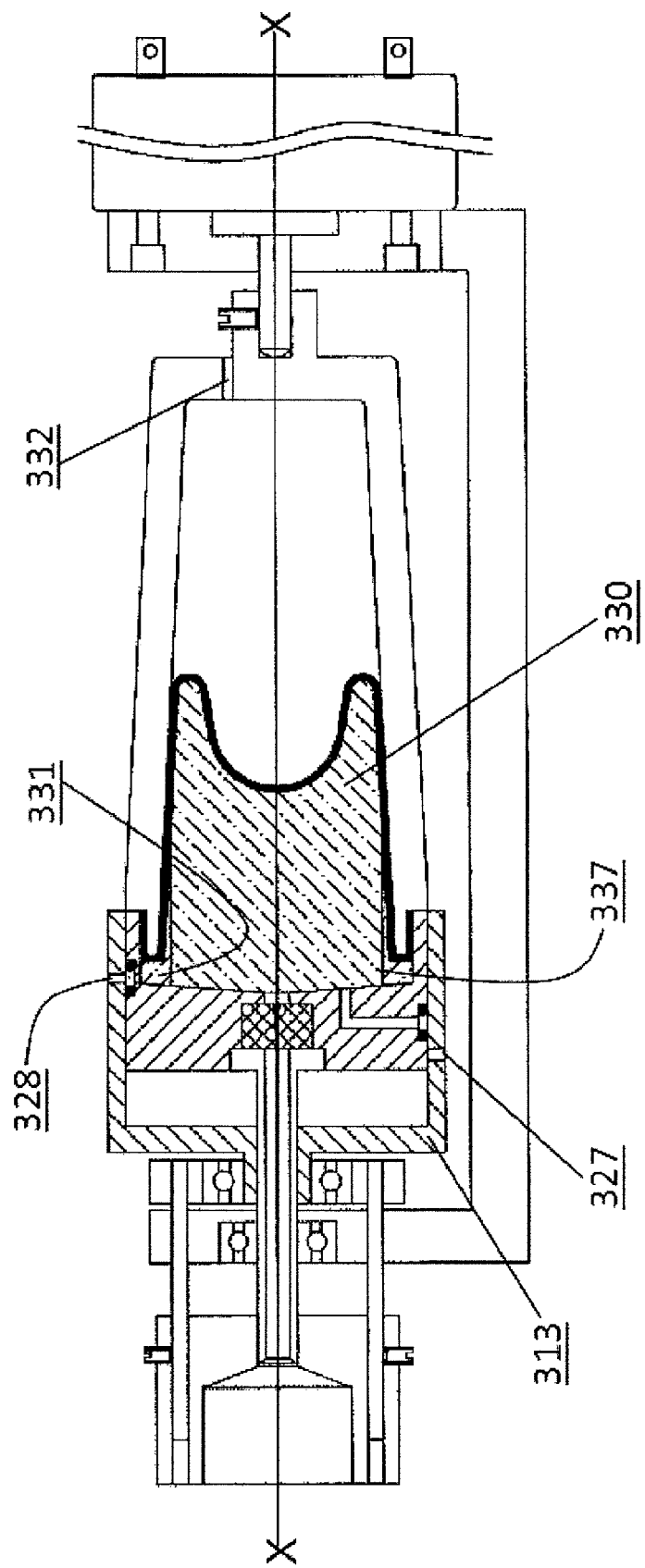

FIG. 10: Centrifuge with bladder chamber, RBCs dumping position, RBC valve open, plasma valve closed (Longitudinal part section)

Figure 11:
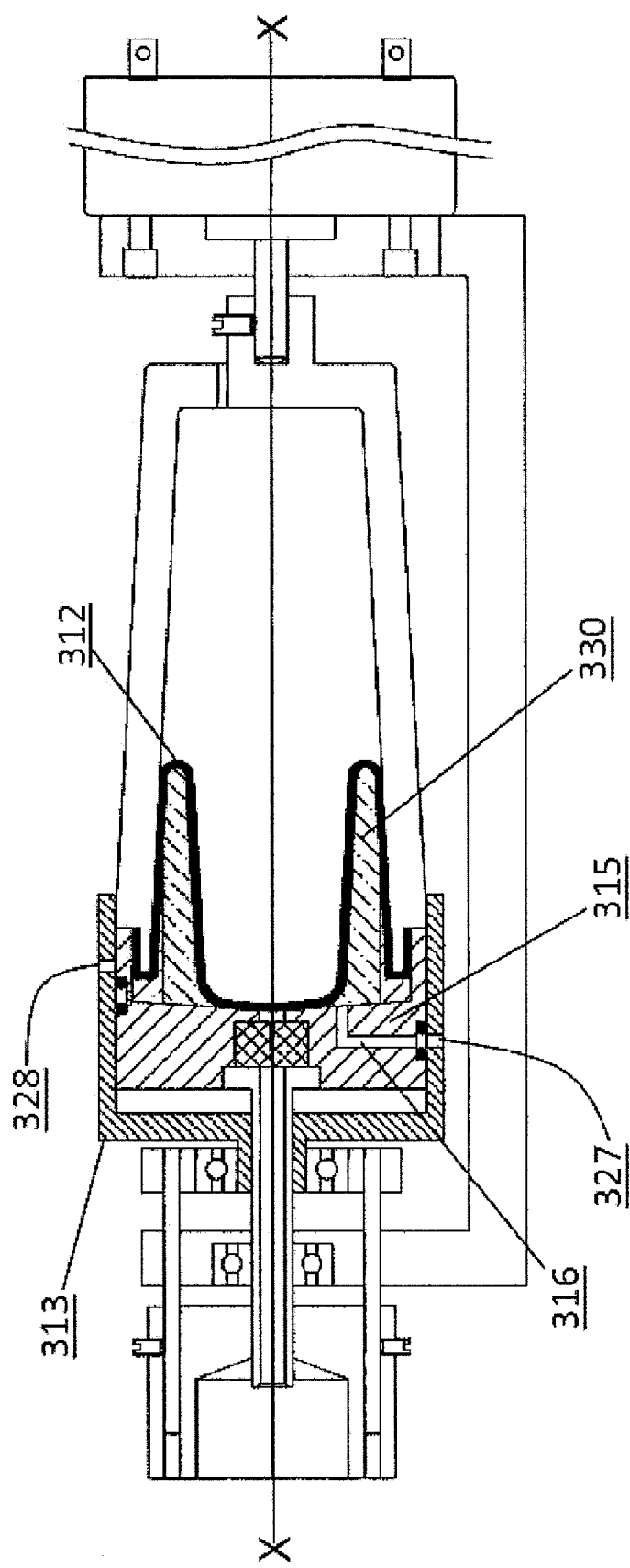

FIG. 11: Centrifuge with bladder chamber, Plasma valve open, RBC valve closed, plasma being dumped (Longitudinal part section)

Figure 12:
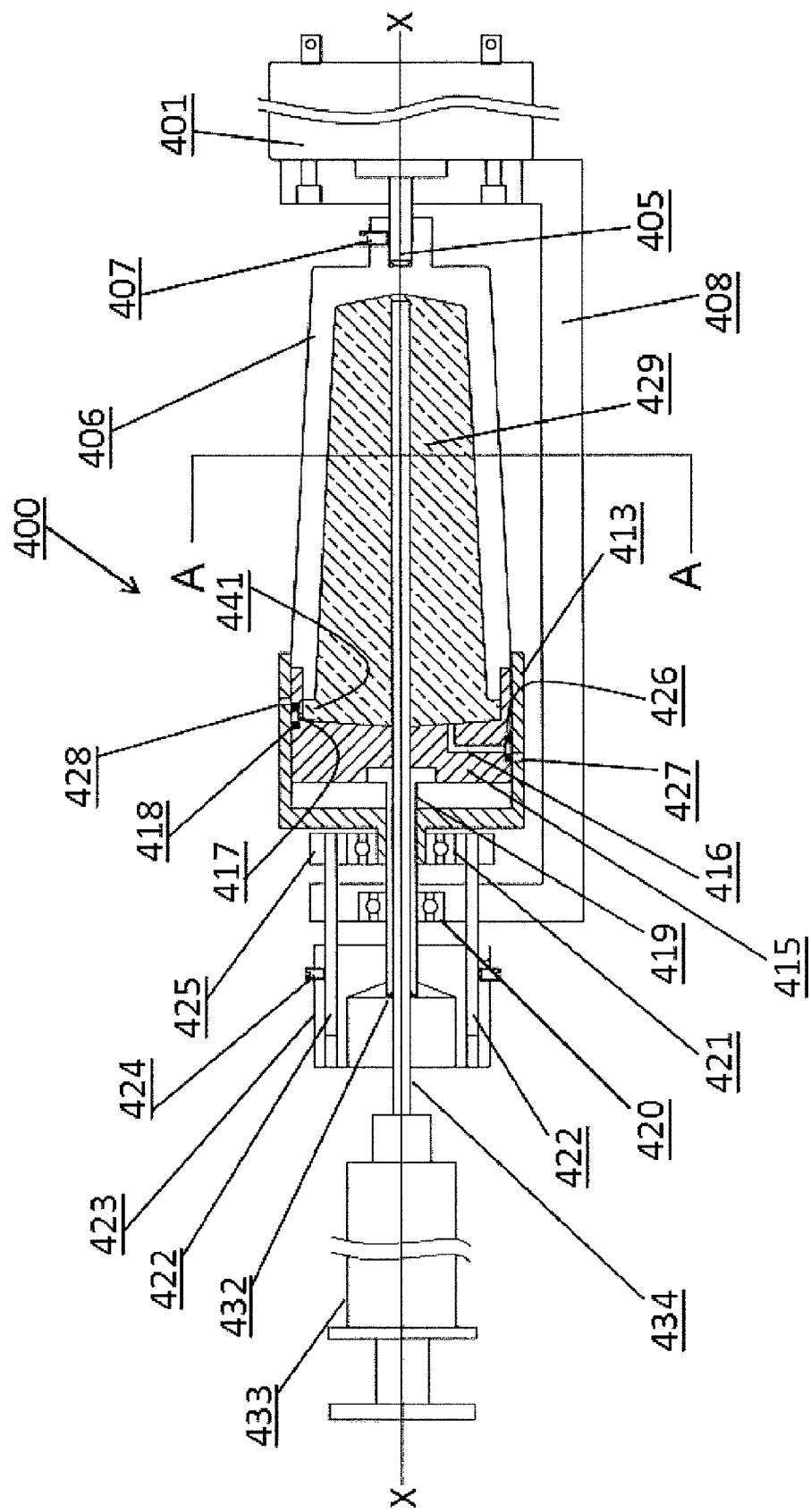

FIG. 12: Centrifuge with air core, initial charge position, both valves closed. (Longitudinal part section)

Figure 13:
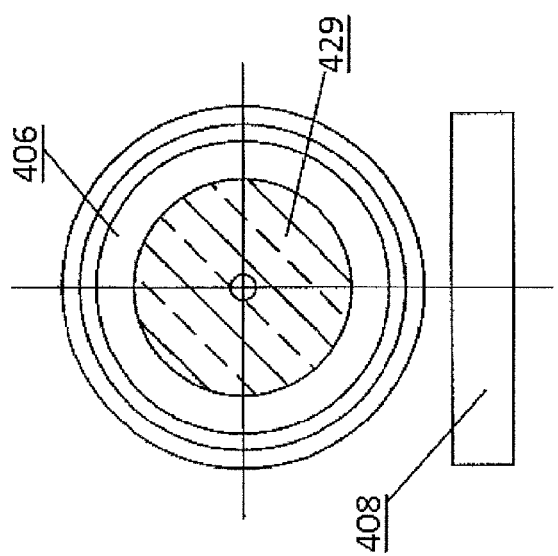

FIG. 13: Centrifuge with air core, (transverse section of FIG. 12.)

Figure 14:
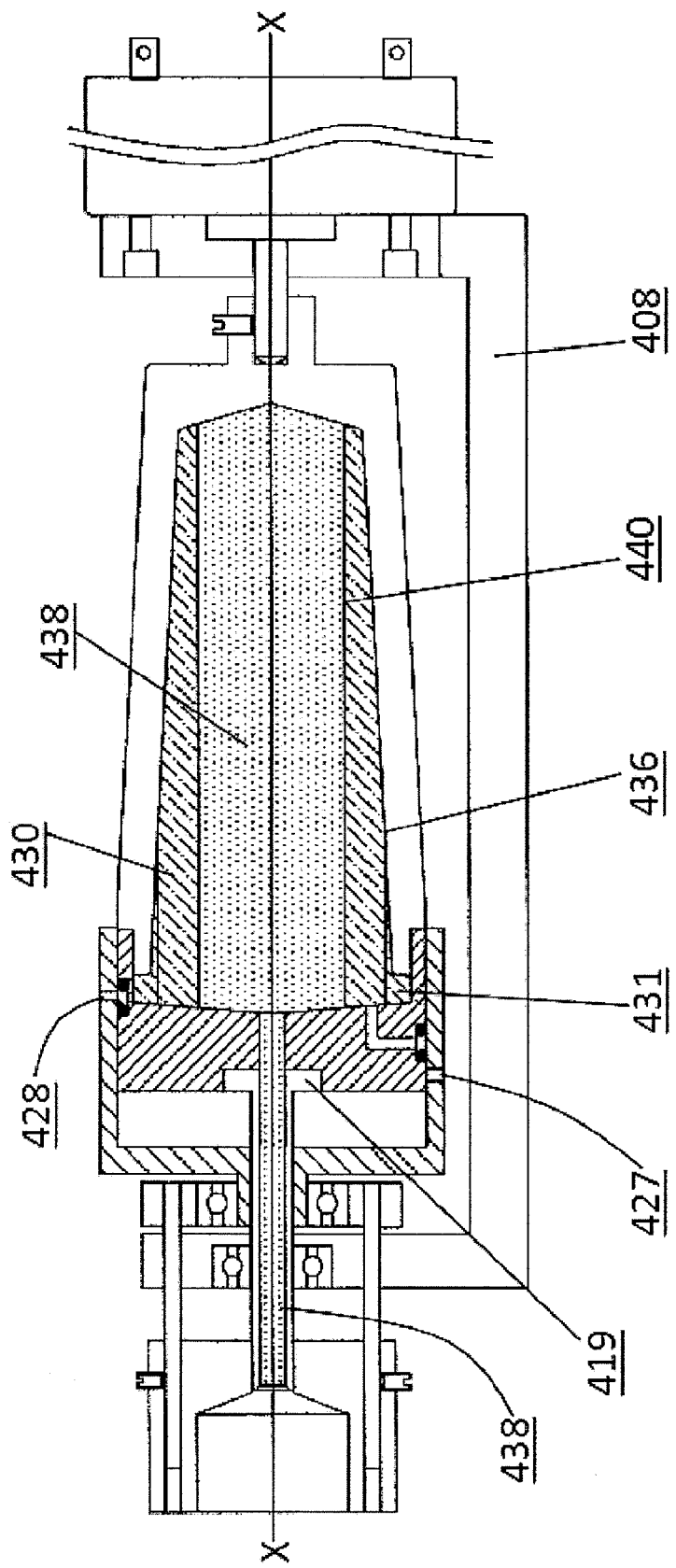

FIG. 14: Centrifuge with air core, spin and separate, RBCs being dumped, RBC valve open, plasma valve closed (Longitudinal part section)

Figure 15:
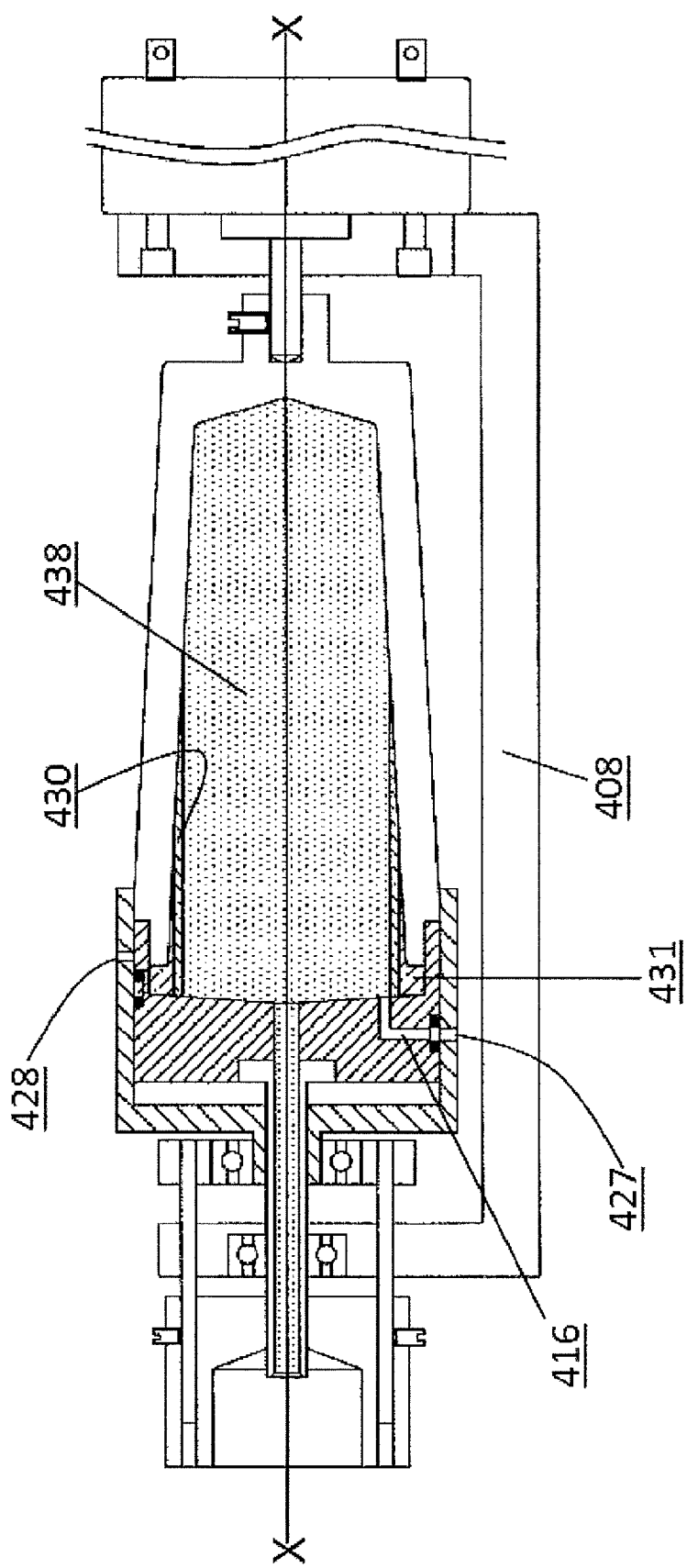

FIG. 15: Centrifuge with air core, RBC valve closed, plasma valve open, residual RBCs and residual plasma remaining (Longitudinal part section)

Figure 16:
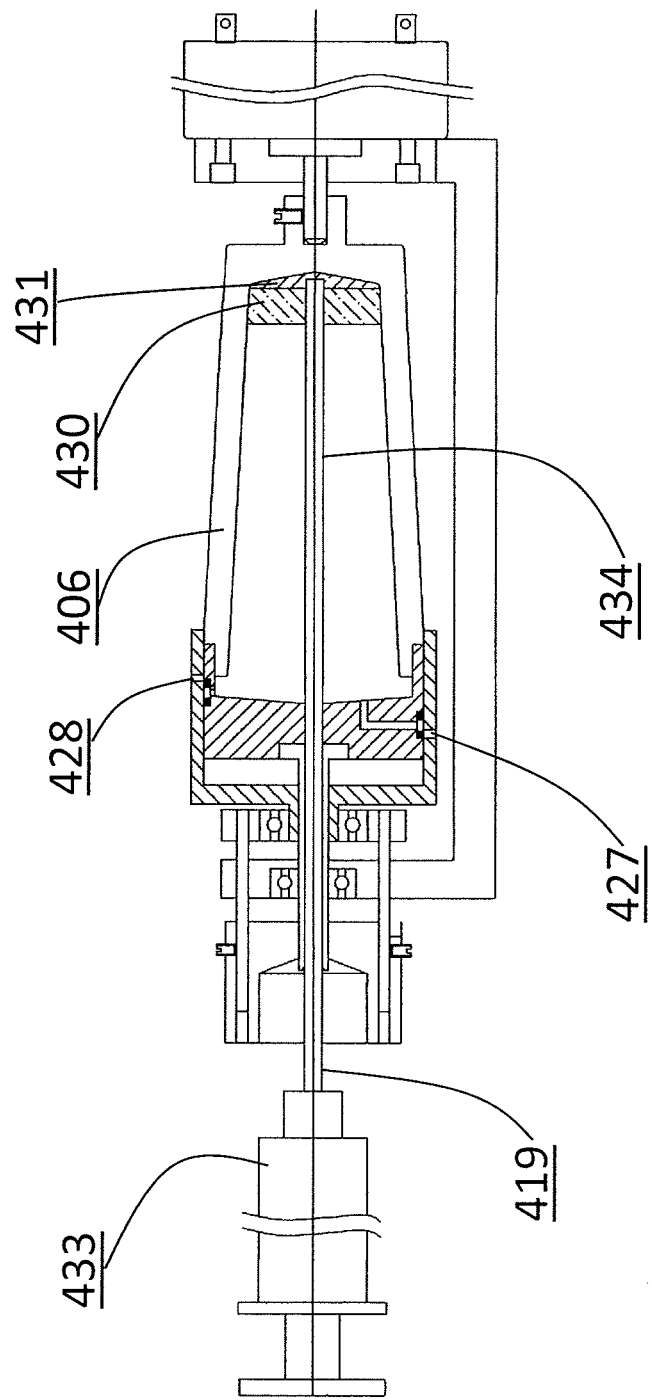

FIG. 16: Centrifuge with air core, removal of PRP at finish, both valves closed (Longitudinal part section)

Figure 17:
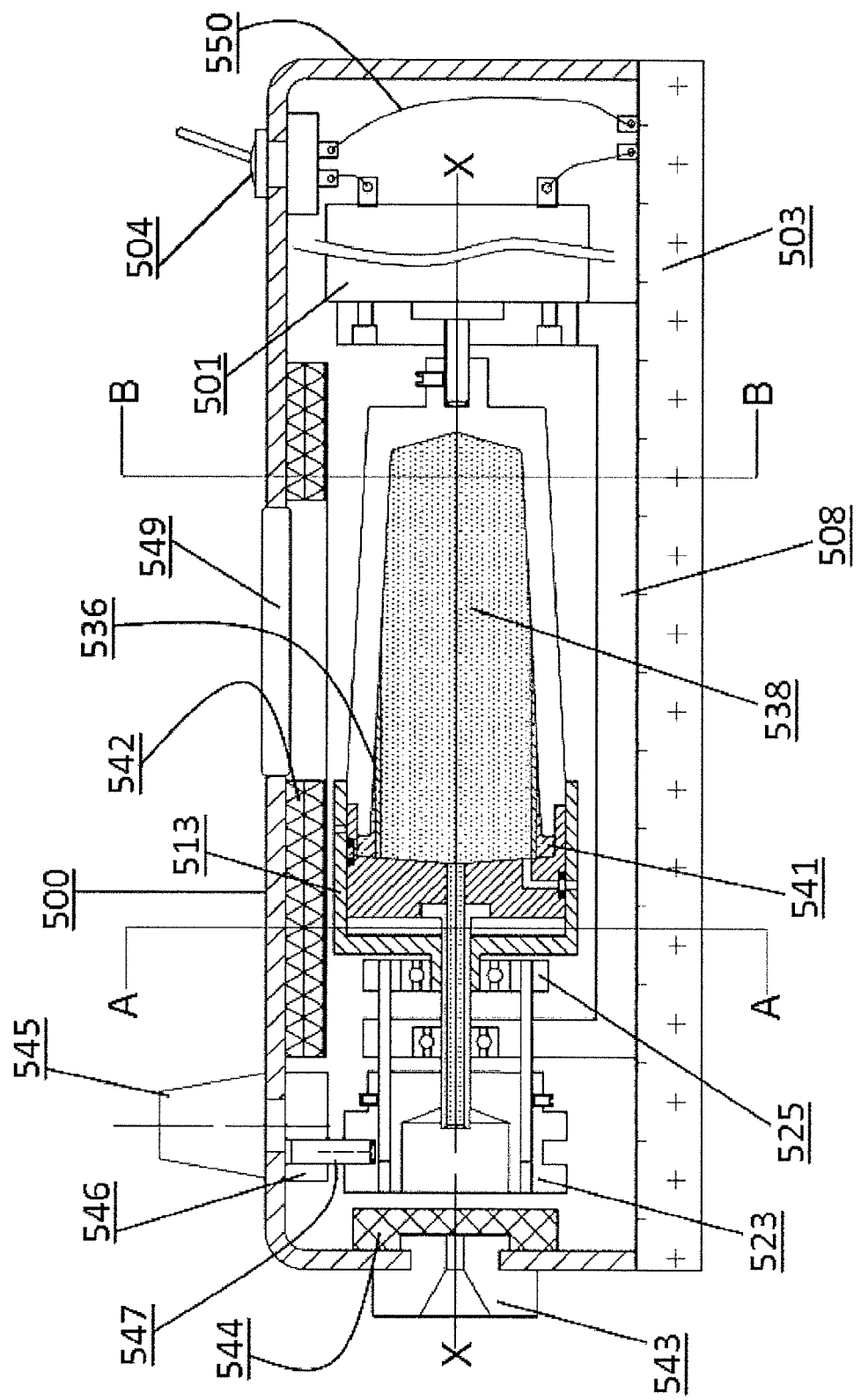

FIG. 17: Centrifuge with a typical enclosure (Longitudinal part section, showing RBC and plasma capture means and aerosol prevention means)

FIGS. 18*a* and 18*b*: Centrifuge with typical enclosure, (transverse section of FIG. 17)

DETAILED DESCRIPTIONS OF THE EMBODIMENTS OF THE INVENTION

FIG. 1*a* provides an illustration for description of the principle of operation of the devices covered in this invention. A chamber of essentially frusto-conical shape 1, contains a mixture of several liquids of differing specific gravities, and rotates about the longitudinal axis XX. The liquids 2, 3, and 4 separate into radially distinct layers as shown in section AA. The taper is beneficial in several ways, first it allows a small volume of liquid to offer a large radial depth (as shown at 11) compared with the radial depth the same volume would have if distributed over the whole length of a right circular cylinder of similar dimensions, see FIG. 1*b* at 14. Second, the taper provides a component of radial acceleration force that helps to scour the outer liquid constituent towards a port 9 placed at the larger cone diameter. Third, the taper also allows visualization of the constituent boundaries as axial locations such as 5 and 6 instead of radial locations such as 7 and 8 in some of the embodiments. In several embodiments the wall 12 of FIG. 1 moves toward the larger diameter and the frusto-conical volume reduces as one or more constituents are ported from the ports, for example at 9 and 10, leaving the center constituent 3 at its original volume. In other embodiments wall 12 remains in place and air is introduced on the center line at 13 to permit the porting of constituents 2 and 4 at 9 and 10 as the air core expands to replace the discharged constituents.

FIG. 2 is a mainly longitudinal section of an essentially circular device, external housing not shown. In FIG. 2 a liquid tight variable volume, the chamber (BSC), is formed from a tapered barrel 206, piston 210, piston seal 211 and end cap 215. Piston 210 and seal 211 are biased toward the larger end of the BSC by spring 209. Larger end of barrel 206 is closed by end cap 215. The inner surface of the end cap 215 forms the larger diameter end wall of the chamber, with the inner surface of the barrel 206 forming the chamber's tapering side wall. In the case where this device is used to enrich plasma from whole blood, end cap 215 has passages 216 and 217 bored within to permit the passage of red blood cells from passage 217 and plasma from passage 216. Passage 217 is shown passing through the outside skirt of the end cap that is in line with the outside wall of tapered barrel 206. A passage bored 90° from that shown at 217; through the inside face of end cap 215 at the maximum ID position would be functionally equivalent to the one shown at 217 and would have a shape similar to passage 216. Passages 217 and 216 connect with valves formed by O-rings 218 compressed in recesses 226 operating in concert with ports 228 and 227 respectively in sleeve 213. These valve components are shown enlarged in FIGS. 3*b* and 3*d*. Sleeve 213 fits slidably on end cap 215 to permit the port holes 228 and 227 to connect with the passages 216 and 217 at appropriate points in the operation. Sleeve 213 is keyed to end cap 215 to permit the transmission of rotary motion between these constituents (key not shown). Insert 219 is fastened to end cap 215 to provide an axle for the ball bearing 220 supporting the left hand end of the rotating assembly. Since the sleeve 213 is rotating with the chamber, a ball bearing 221 is provide to connect the sleeve to a non-revolving knob 223 via collar 225 and rods 222. The knob and sleeve can be placed in 3 positions: first position, port 228 open and port 227 closed: second position, both ports 227 and 228 closed: third position, port 228 closed and port 227 open. Barrel 206 is fastened to the shaft 205 of electric motor 201 using screw 207. No additional bearings are provided at the motor end, the motor bearings sufficing to support the barrel. The complete assembly is supported by a frame 208, the insert bearing 220 and the motor 201 being located on this same frame. The rotating components all rotate about axis XX.

To use the device for preparing PRP, a syringe 233 with needle 234, filled with anti-coagulated whole blood is inserted into the device through elastomeric seal 214 to load the chamber with whole blood 229. Knob 223 is placed in the first position to allow air to discharge from port 228 as the chamber is filled with blood. Whole blood 229 fully charges the chamber pushing the piston 210 and seal 211 to the far right, compressing spring 209.

FIG. 3*a*, a cross section at AA in FIG. 2, clarifies the construction of the knob 223 and rod components 222. FIG. 3*b* is a cross section at BB in FIG. 2 showing details for the valve components, those being the recess 226 in end cap 215, O-ring 218 and port 228 in sleeve 213 (the construction of the valve for port 227 is the same). FIG. 3*c* shows the section at CC of FIG. 2.

Once the chamber has been charged with whole blood, the knob and sleeve are placed in the second position with both valves closed, the syringe 223 is removed and the motor started. The motor is then run for times between 15 and 90 seconds depending on the speed used. Speeds of 10,000 rpm to 25,000 rpm have been used, developing centrifugal accelerations at the outside of the spinning chamber from 1000 g to 6000 g.

FIG. 4 shows the device of FIG. 2 in operation rotating at speed. The RBC port 228 and the plasma port 227 are both closed. The boundary between the RBC layer and the plasma layer is shown at 237. The piston 210 is still at the as-charged position and the spring 209 is fully compressed. The spring has two functions, it moves the piston to the left as red blood cells are discharged from the chamber through port 228, and the spring creates a significant minimum pressure in the revolving liquid: this prevents the core of the spinning liquid from reaching the vapor pressure of the liquids and may suppress cell damage in some circumstances.

Once the red blood cells and the plasma have separated, with the device still rotating, the knob and sleeve are placed in the first position and red blood cells are discharged from port 228 into the casing (casing not shown, but see FIGS. 17 and 18) surrounding the device. FIG. 5 shows the situation at the mid-point of the RBC 231 discharge when the piston 210 is in mid position. Once the majority of red blood cells have been discharged the valve is placed in the third position and plasma 230 is eliminated from port 227. FIG. 6 shows the situation at the end of the enrichment process: the plasma port 227 is still open and the piston is close to the far left position: platelets that have a specific gravity between that of plasma and RBCs are trapped at the RBC-plasma boundary layer 237; the plasma port is about to be closed and the motor stopped.

Typical volumes for the chamber are 20-100 mL, and the amount of enriched plasma removed at the termination of the procedure is approximately a quarter to an eighth of the original volume depending on the degree of enrichment desired.

In order to retain all the platelets and other factors gathering at the RBC-plasma boundary, it is essential to close port 228 before all the RBCs have been removed, otherwise there is the danger of these constituents flowing out with the last RBCs. To ensure that this does not occur, the blood sample hematocrit value is used to judge the residual volume of the chamber when the RBC port must be closed. This volume is observable as a piston axial position, and the valve is moved from position one to position three as the piston reaches this predetermined position.

The device described in FIGS. 2 through 6 uses a piston and seal traveling in a tapered tube, but a right circular cylinder may well function adequately for mixtures of liquids other than blood and where the residual volume of the first liquid discharged is not too critical. The tapered tube has the advantages mentioned in the discussion of FIG. 1. The position of the piston can be judged visually by the operator relative to graduations on the barrel (not shown), or an optical detector and automatic valve operation system can be used (not shown)

Since the residual enriched plasma is injected back into the patient the materials used for this device have to be medical grade materials, at least for those constituents contacting the blood. Polycarbonate or PTE are suitable for the barrel 206, end cap 215, sleeve 213, frame 208, knob 223 and collar 225. Insert 219 is of a suitable grade of passivated stainless steel such as 416 or 420. The ball bearings have to do duty at high speed but operate for very short times so stainless steel bearings of grade ABMA 1-3 are adequate. O-rings 218 and seal 211 are of silicone rubber. Since the motor does not contact blood industrial motors (for example those made by Mabucci) are adequate.

FIG. 7 shows an embodiment with a flexible bladder 312 that initially conforms to the bore of the barrel 306, the bladder providing a variable volume chamber through its ability to invert as shown in FIGS. 10 and 11. This embodiment may serve to reduce the effect of entrapped air bubbles.

In FIG. 7 a liquid tight variable volume centrifuge chamber (the BSC) is formed from a tapered barrel 306 containing a molded bladder 312, and end cap 315. The bladder is captured in a return fold 339 between a barrel projection 338 and the end cap 315. Larger end of barrel 306 is closed by end cap 315. In the case where this device is used to enrich plasma from whole blood, end cap 315 has passages 316 and 317 bored within to permit the passage of red blood cells from passage 317 and plasma from passage 316. Passages 317 and 316 connect with valves formed by O-rings 318 compressed in recesses 326 operating in concert with ports 328 and 327 respectively in sleeve 313. Sleeve 313 fits slidably on end cap 315 to permit the ports 328 and 327 to connect with the passages 316 and 317 at appropriate points in the operation. The knob 323 and sleeve 313 can be placed in 3 positions: first position, port 328 open and port 327 closed: second position, both ports 327 and 328 closed: third position, port 328 closed and port 327 open. Sleeve 313 is keyed to end cap 315 to permit the transmission of rotary motion between these constituents (key not shown). Insert 319 is fastened to end cap 315 to provide an axle for the ball bearing 320 supporting the left hand end of the rotating assembly. Since the sleeve 313 is rotating with the chamber a ball bearing 321 is provide to connect the sleeve to a non-revolving knob 323 via collar 325 and rods 322. Barrel 306 is fastened to the shaft 305 of electric motor 301 using screw 307. No additional bearings are provided at the motor end, the motor bearings sufficing to support the barrel. The complete assembly is supported by a frame 308, the insert bearing 320 and the motor 301 being located on this frame. The revolving components all rotate about axis XX. In this illustration the sleeve is in the first position to keep the port 328 open for porting of air as the chamber is charged with blood, and the plasma port 327 is closed. Whole blood 329 fully charges the chamber. An elastomeric seal 314 permits the introduction of a needle 334 for the passage of whole blood into the chamber before the start of rotation, and removal of enriched plasma at the cessation of action.

FIG. 8 is a transverse cross section of the device shown in FIG. 7 at section AA. Whole blood 329 fills the BSC and bladder 312 which is fully in contact with barrel 306. Frame 308 runs under the rotating assembly.

FIG. 9 shows the device of FIG. 7 in operation rotating at speed. The sleeve 313 is in position two with both ports 327 and 328 closed. The boundary between RBCs 331 and plasma 330 is shown at 337. The bladder is still against the barrel now under the influence of the pressure developed by the spinning liquid mixture.

FIG. 10 depicts the situation after spinning for 60 seconds or so. The sleeve 313 is placed in position one, port 328 is open and RBCs 331 are being discharged through port 328. Plasma port 327 is closed. The bladder has moved to the left to compensate for the volume of RBCs that have been discharged. The shape adopted by the bladder is a balance between the forces developed by liquid pressure pushing the bladder to the right and atmospheric pressure (via vent 332) pushing the bladder to the left. Since the pressure at the center of the spinning liquid is near absolute zero the atmospheric pressure exceeds the left hand pressure that has been developed up to a certain radius, hence the re-entrant shape of the bladder. The volume of plasma 330 has remained the same as when introduced. The boundary between RBCs and plasma is shown at 337. In this view the RBC discharge is about to be stopped since the residual RBC volume 331 is low enough.

FIG. 11 illustrates the final position for the bladder 312 while the rotation continues but just prior to stopping. Sleeve 313 is in position three, RBC port 328 is closed and plasma port 327 is still open. Plasma has been discharged through port 327 and is about to be cut off by the bladder rolling onto end cap 315 and cutting off the passage 316. This illustrates the minimum volume of enriched plasma 330. At this point the sleeve 313 is moved to position two with both ports closed and the rotation is then stopped; the residual liquid is removed using a syringe in a similar manner to the charging described in FIG. 7.

Materials for the device of FIGS. 7 through 11 are similar to those for the device of FIGS. 2 through 6: the bladder by example can be made of silicone rubber, polyurethane or polyvinylchloride.

For the previous device 200 the piston position provided the signal for closure of the RBC port 328. In the case of the bladder the inverted bladder rolls along the tapered barrel bore, the axial position of the reverse edge providing (labeled 312 in FIG. 11) the volume and the signal for port closure. The cut-off of the plasma discharge is automatic as the bladder rolls over the port passage 316.

The device described in FIGS. 12 through 16 utilizes an air core and uses no bladder or piston.

The device of FIG. 12 is very similar in construction to the two previous embodiments, with a BSC formed from a barrel 406 and end cap 415. The inner surface of the end cap 415 forms the larger diameter end wall of the chamber, with the inner surface of the barrel 406 forming the chamber's tapering side wall. In this illustration whole blood 429 from syringe 433 fills the centrifuge chamber through needle 434 with both ports 428 and 427 closed. Air displaced by the blood leaks out through the clearance between the needle 434 and insert 419 bore as the blood is injected. FIG. 13 shows the circular section nature of FIG. 12. Once the charging syringe is removed, the motor is started and the chamber is rotated at 10,000 to 20,000 rpm for approximately one minute. At this point the sleeve 413 is moved to the second position, and RBCs are discharged through port 428 until the point shown in FIG. 14 where the minimum RBCs 431 remain. Meanwhile, the plasma adopts the region or layer 430, and a boundary 440 forms at the plasma-air radial interface, the air core 438 having entered through the bore of insert 419 (via a filter in the housing not shown, but see FIGS. 17 and 18). At this juncture the sleeve is moved to the third position, port 428 closed and port 427 opened. With this preferred device there is no bladder or piston to observe, so the operator observes the axial interface 436 between the RBCs 431 and the plasma 430 of the mixture through the transparent barrel to determine when to manually close the RBC port 428 and open the plasma port 427. With blood, this mixture interface is easy to see and can be automated with an optical detector. The difference in electrical resistivity between red blood cells and plasma can also be used to trigger an indicator or automated valve. An alternative way of determining the point at which to shut the RBC port is to use time. After one minute of running to separate the constituents of the blood, the RBC port is opened and a timer started. Since the pressure generated in the centrifuge is a predictable function of liquid specific gravity and running speed, and since the RBC port is a precisely calibrated orifice, the flow rate being discharged, and hence time can be computed for a given hematocrit value.

With the motor still running, the plasma discharges through port 427 until it reaches the situation in FIG. 15 where the residual RBCs are at layer 431 and the residual plasma at layer 430. The sleeve is then moved to the second position to close both ports. In the case of plasma the passage 416 is placed at a precise radial location to give an accurate final volume since no further flow of plasma will occur once the air core 438 has grown to that passage radial location. The motor is then stopped and the device placed on end, with the motor downward, so that the rotation axis is vertical as shown in FIG. 16. The remaining enriched plasma with some RBCs is removed by syringe and needle as illustrated.

An enclosure suitable for all embodiments discussed in this application is described in FIGS. 17 and 18; however these two figures show the enclosure applied specifically to the air core embodiment of FIGS. 12 through 16. The frame 508 is mounted to a battery power pack 503 that acts as the base for the enclosure. An outer casing 500 surrounds the centrifuge and is fastened to the battery pack 503, the joint being liquid and air-tight. A valve selector knob 545, integral with eccentric 546 and pin 547, is mounted in the casing such that the selector knob 545 can be turned by the operator to actuate the internal knob 523 via the pin 547 in groove 548 and hence the collar 525 and valve sleeve 513. In FIG. 17 the motor 501 driving the chamber BSC is controlled manually by switch 504 connected to battery pack 503 by wires 550. A bush 543 mounted at the left hand end of the enclosure 500 provides alignment for the entry of the syringe (433 FIG. 12) needle when charging the chamber with whole blood or when extracting the enriched plasma. Immediately adjacent to bush 543 is a porous flexible pierceable filter 544. This filter has two functions: It filters the air entering the core of the centrifuge when it is running, and it prevents the egress of any aerosols into the atmosphere of blood fragments generated as the centrifuge discharges RBCs or plasma into the casing. A small slit in the filter allows the charging syringe needle to enter without damaging the effectiveness of the filter. Covering most of the interior walls of the casing 500 is a highly absorbent lining 542 to absorb the RBCs and plasma discharged into the casing as the air core 538 enlarges and the enrichment process proceeds. A lens and mask 549 placed in the wall of the casing 500 permits the operator to view the axial interface 536 of the RBCs and plasma as the process of enrichment proceeds. The mask and lens are chosen to enhance the contrast of the image seen of the liquid separation interface 536.

A photo detector (not shown) can be placed in the location of the lens to provide an electrical signal of the progress of the liquid separation interfaces, and an electromagnet actuator can drive the valve selector knob 545. These electrical elements in conjunction with a manual switch can be used to control the entire process once the motor has started.

From tests to date it would seem feasible in some applications to use a simple timer program to schedule the sleeve motions. For example, the following sequence can operate off a timer once the chamber is charged with blood, a) start motor, run for 60 seconds b) open RBC port and discharge RBCs for 30 seconds, c) close RBC port and open plasma port and run for 30 seconds, d) close both ports, and stop motor. Such a device might require the addition of a means of manually inserting the patient's hematocrit number to allow for varying proportions of RBCs to plasma.

Table 1 gives typical data obtained for the air core device of FIGS. 12 through 16 using porcine blood. The data was obtained with runs of one minute for the initial separation and approximately one more minute to discharge the RBCs and plasma.

TABLE 1

| Sample | Platelet Count ($\times 10^3$/microliter) | Platelet Concentration Factor | % Platelet Recovery | % Red Blood Cells Removed |
|---|---|---|---|---|
| Baseline | 229 | NA | NA | NA |
| Run 1 | 1656 | 7.2 | 100 | 93 |
| Run 2 | 1457 | 6.4 | 88 | 92 |
| Run 3 | 1446 | 6.3 | 87 | 93 |
| Run 4 | 1685 | 7.3 | 100 | 94 |

For all three embodiments discussed, piston, bladder and air core, the size and position of the ports and passages are very important. As the centrifuge rotates, the pressure developed within the chamber varies as the square of the speed and the square of the radius of rotation. To gain manual control over the discharge of constituents the discharge needs to take place over a manageable time. The RBC port for example needs to be sized to allow passage of the RBCs over a period of about 30 seconds. Conditions must be selected to allow the RBC port to function without blockage as the RBCs try to clump, and flow has to be kept low enough to stop the platelets from being swirled into the exit vortex. For centrifuges using whole blood samples of approximately 30 mL, it has been found that RBC ports of the order 0.008 inch diameter work well if speeds are in the region 15,000 to 20,000 rpm and chamber barrels are about 1.0 to 1.25 inch in diameter at the largest point. Plasma ports can be larger since the risk of losing the platelets is less: values of about 0.010 inch diameter are adequate. Placement of the plasma ports relative to the center axis of rotation has a direct effect on the attainable concentration factor. The closer to the center, the less plasma is removed and less concentration is achievable. Additionally, in all embodiments of the invention discussed it will be noticed that a small annulus 241, 341, 441, 541 is created at the large diameter end of the chamber. This annulus creates a localized area of increased radial depth, but of small volume, for the RBCs prior to their entry into the RBC passages 217, 317, 417. This increase in depth reduces the tendency for the platelets and other desired factors from exiting with the RBCs being discharged through the RBC port 228, 328, 428 under influence of the exit vortex created locally close to the same ports (not shown).

In all the embodiments discussed the accuracy of the RBC port closure point can be improved by employing a flowable separator gel of an intermediate density between the red blood cells and the platelets. The separator gel spreads over the red blood cell layer moving the other layers further towards the center axis. The separator gel automatically caps the first port when all of the red blood cells have exited. The separator gel viscosity is designed so that it will not pass through the small exit port at the centrifuge speed employed in the BSC. The automatic shut off of the first port can also be accomplished with a solid material of intermediate specific gravity that is designed to enter and close off the port when the red blood cells have fully exited. An example would be plastic beads such as microspheres with the desired intermediate specific gravity that are large enough to cap the port when agglomerated as they flow toward the port.

For the bladder and air core embodiments the visualization of the RBC plasma axial boundaries can be improved by incorporating back lighting in the form of an LED mounted inside the BSV adjacent to the motor centerline. Additional windings in the motor could provide the low power needed to power the lamp.

With adjustments to size and locations of the port and passage dimensions, the subject invention also has the capability for separating and concentrating a wide variety of therapeutically beneficial cells and other biological constituents. Many of these biological constituents have the potential for regenerative therapy and can be characterized as regenerative agents. These regenerative agents can assist with the regeneration, restoration, or repair of a structure or assist with the function of an organ, tissue or physiologic unit or system to provide a therapeutic benefit to a living being. Examples of regenerative agents include for example: stem cells, fat cells, progenitor cells, bone marrow, synovial fluid, blood, endothelial cells, macrophages, fibroblasts, pericytes, smooth muscle cells, uni-potent and multi-potent progenitor and precursor cells, lymphocytes, etc. The invention also has the potential to process soft or liquid tissues or tissue components or tissue mixtures including but not limited to adipose tissue, skin, muscle, etc. to provide a therapeutic regenerative agent.

The blood centrifuge container may also incorporate an adjustable port, e.g. a tube with an open end extending radially into the BSC and hinged at the outer periphery in such a manner that the tube can be swung in an arc for the open end to scan a range of radii (not shown). The location of the open end of the tube can be adjusted before or during operation such that it is located at a desired position with respect to the axis of rotation. For example, the entrance port could be located towards the periphery of the centrifuge container to initially vent undesired cells, and later adjusted towards the center of the container to vent platelet poor plasma. Alternatively, if the plasma fraction is what is desired to be removed, the port can be positioned so that essentially only plasma is tapped from the stratified mixture.

The apparatus may also be configured to shut off, or at least to cease rotating, once a predetermined quantity of one or more constituents such as plasma has been tapped. Specifically, a port may be positioned such that, upon stratification, the plasma constituent is adjacent the port. When the valve for that port is opened, plasma is dispatched out through the port. The port may also be configured with a sensor that senses the presence or absence of plasma. As such, the apparatus can be configured such that the barrel continues to rotate as long as plasma is sensed at or in the port, but when plasma is no longer sensed, the sensor provides a signal to the motor to stop (thereby stopping the rotation of the barrel) or signaling the opening of a tap. As plasma continues to be removed from the barrel through the port, eventually the supply of plasma at the radius of the port is exhausted, thereby causing a signal to be sent from said sensor, and the barrel stops rotating. Of course, each of these signals may arise from the sensing of any stratified layer, not just plasma.

It may be desirable to collect one or more of the discarded fractions of the liquid specimen in addition to the concentrated fraction. This can be accomplished by one of several methods. A collection bag or chamber can be connected to an exit port on the sleeve. This bag or chamber will rotate with the barrel so provisions must be taken to balance it around the axis of rotation. Another method would be to have a circumferential funnel opposite the desired exit port that would collect the fraction being discharged and guide the fluid to a collection point by gravity flow.

The invention claimed is:

1. A centrifuge for selectively concentrating and collecting constituents of a biologic liquid mixture, said constituents having differing specific gravities and being stratifiable in a centrifugal field produced by said centrifuge, said centrifuge comprising:
  a) a chamber arranged to contain a liquid mixture and having a central longitudinal axis about which said chamber is arranged to be rotated to produce said centrifugal field, said chamber comprising:
    (i) an assembly comprising a tubular barrel and an end wall, each comprising a common central longitudinal axis, said tubular barrel comprising a side wall tapering radially inward toward said central longitudinal axis from said end wall, said side wall comprising a transparent material;
    (ii) an inlet for adding the liquid mixture to said chamber;
    (iii) a first port in fluid communication with said chamber and located in said assembly at a first predetermined radius from said central longitudinal axis; and
    (iv) a second port in fluid communication with said chamber;
  b) a motor to rotate said chamber about said central longitudinal axis to produce said centrifugal field, whereupon said constituents of said biologic liquid mixture in said chamber stratify into at least two concentric stratified constituent layers as a function of the differing specific gravities of said constituents, said at least two concentric stratified constituent layers forming an interface between immediately adjacent constituent layers thereof, said interface being visible through said transparent side wall, and wherein a first of said at least two concentric stratified constituent layers is present at said first port, said first port being selectively openable to enable at least a portion of said first of said at least two concentric stratified constituent layers to be automatically ejected from said chamber through said first port as a result of pressure built up by said centrifugal field; and
  c) an actuatable member arranged to be actuated in response to the observation of said interface to close said first port.

2. The centrifuge of claim 1, additionally comprising a vent to permit air to enter said chamber to at least partially replace a volume of said stratified constituent layer ejected from said chamber.

3. The centrifuge of claim 1, additionally comprising a valve coupled to said first port and wherein said valve is responsive to a first signal.

4. The centrifuge of claim 3, wherein said first signal is arranged to be produced in response to the actuation of said actuatable member to cause said valve to close said first port.

5. The centrifuge of claim 1, additionally comprising a detector for detecting said interface and for providing a first signal in response thereto.

6. The centrifuge of claim 1, wherein a second of said at least two concentric stratified constituent layers is present at said second port, said second port being located in said assembly at a second predetermined radius from said central longitudinal axis and wherein said second port is selectively openable to enable at least a portion of said second of said at least two concentric stratified constituent layers to be automatically ejected out of said chamber through said second port by said centrifugal field.

7. The centrifuge of claim 1, whereupon the ejection of at least a portion of said first of said at least two concentric stratified constituent layers out of said chamber through said first port leaves a residual portion of said biologic liquid mixture in said chamber and wherein said chamber additionally comprises another port for enabling the removal of at least a portion of said residual portion of said biologic liquid mixture from said chamber through said another port.

8. The centrifuge of claim 5, wherein said detector detects said interface on the basis of visual differences between said immediately adjacent stratified constituent layers.

9. The centrifuge of claim 5, wherein said detector detects said interface on the basis of differences in electrical conductivity between said immediately adjacent stratified constituent layers.

10. The centrifuge of claim 1, wherein the maximum diameter of said chamber and the volume of said chamber are sufficiently small and the rotational speed of said chamber is sufficiently high so that said constituents of said biologic liquid mixture in said chamber stratify into said at least two concentric stratified constituent layers having a thickness of no more than approximately 0.5 inch in approximately 90 seconds or less, with a first of said at least two concentric stratified constituent layers being present at said first port.

11. The centrifuge of claim 1 wherein the biologic liquid mixture is a plasma-containing liquid mixture and wherein said centrifuge additionally comprising a sensor associated with said second port, said second port being located in said assembly at a second predetermined radius from said central longitudinal axis, said second predetermined radius being less than said first predetermined radius, said second port being selectively openable to enable at least a portion of plasma from the plasma-containing liquid mixture to be automatically ejected out of said chamber through said second port by said centrifugal field, said sensor being arranged for detecting the absence of plasma thereat and providing a signal to automatically stop rotation of said chamber when an absence of plasma at said second port is sensed.

12. The centrifuge of claim 1 wherein said actuatable member is arranged to be manually actuated by an human operator upon the visualization of said interface at a desired position in said chamber, said first port being sized such that said automatic ejection of at least a portion of said first of said at least two concentric stratified constituent layers occurs over a time span of suitable duration such that the human operator can determine with precision when said interface is at the desired position, and wherein a second of said at least two concentric stratified constituent layers present at said second port after closing of said first port, said second port being selectively openable after closing of said first port to enable at least a portion of said second of said at least two concentric stratified constituent layers to be automatically ejected from said chamber through said second port as a result of pressure built up by said centrifugal field, whereupon a desired constituent of the biologic liquid remains in said chamber for subsequent removal.

13. The centrifuge of claim 12 additionally comprising a valve for effecting the selective opening and closing of said first port, said valve being arranged to be manually opened and closed by the human operator.

* * * * *